US012171557B2

(12) United States Patent
Rastogi et al.

(10) Patent No.: US 12,171,557 B2
(45) Date of Patent: Dec. 24, 2024

(54) ASSESSEMENT OF PERFORMANCE OF AN IMPLANTED SENSOR

(71) Applicant: Senseonics, Incorporated, Germantown, MD (US)

(72) Inventors: Ravi Rastogi, Columbia, MD (US); James Masciotti, Germantown, MD (US); Xiaoxiao Chen, Washington, DC (US)

(73) Assignee: Senseonics, Incorporated, Germantown, MD (US)

( * ) Notice: Subject to any disclaimer, the term of this patent is extended or adjusted under 35 U.S.C. 154(b) by 0 days.

(21) Appl. No.: 18/353,567

(22) Filed: Jul. 17, 2023

(65) Prior Publication Data

US 2023/0355148 A1 Nov. 9, 2023

Related U.S. Application Data

(62) Division of application No. 16/709,225, filed on Dec. 10, 2019, now Pat. No. 11,701,038.

(Continued)

(51) Int. Cl.
*A61B 5/145* (2006.01)
*A61B 5/07* (2006.01)
*A61B 5/1495* (2006.01)

(52) U.S. Cl.
CPC ............ *A61B 5/1495* (2013.01); *A61B 5/076* (2013.01); *A61B 5/14503* (2013.01);

(Continued)

(58) Field of Classification Search
CPC .... A61B 2560/0271; A61B 2560/0276; A61B 5/076; A61B 5/14503; A61B 5/14532;
(Continued)

(56) References Cited

U.S. PATENT DOCUMENTS 6,895,263 B2  5/2005  Shin et al.
8,515,516 B2  8/2013  Kamath et al.
(Continued)

FOREIGN PATENT DOCUMENTS

EP    2335584 A2   6/2011
EP    2305105 B1   5/2012
(Continued)

*Primary Examiner* — Eric J Messersmith
(74) *Attorney, Agent, or Firm* — Rothwell, Figg, Ernst & Manbeck, P.C.

(57) ABSTRACT

An analyte monitoring system and method. The analyte monitoring system may include an analyte sensor and a transceiver. The analyte sensor may include an analyte indicator that exhibits one or more detectable properties based on an amount or concentration of an analyte in proximity to the indicator. The transceiver may be configured to receive one or more measurements from the sensor. The transceiver may be configured to assess in real time a performance of the sensor based on at least the one or more measurements. The transceiver may be configured to determine whether the performance of the sensor is deficient based at least on the assessed performance of the sensor. The transceiver may be configured to calculate an analyte level based on at least the one or more sensor measurements. The transceiver may be configured to determine whether the calculated analyte level is a spike.

18 Claims, 6 Drawing Sheets

Related U.S. Application Data

(60) Provisional application No. 62/777,591, filed on Dec. 10, 2018.

(52) U.S. Cl.
CPC ... *A61B 5/14532* (2013.01); *A61B 2560/0271* (2013.01); *A61B 2560/0276* (2013.01)

(58) Field of Classification Search
CPC .... A61B 5/1495; A61B 5/0031; A61B 5/7221
See application file for complete search history.

(56) References Cited

U.S. PATENT DOCUMENTS

| | | |
|---|---|---|
| 9,211,092 B2 | 12/2015 | Bhavaraju et al. |
| 9,289,179 B2 | 3/2016 | Hayter et al. |
| 9,414,775 B2 | 8/2016 | Colvin, Jr. et al. |
| 9,693,714 B2 | 7/2017 | DeHennis et al. |
| 9,736,210 B2 | 8/2017 | Root et al. |
| 9,743,872 B2 | 8/2017 | Hayter et al. |
| 9,833,199 B2 | 12/2017 | Johnson et al. |
| 9,949,678 B2 | 4/2018 | Fennell et al. |
| 10,111,609 B2 | 10/2018 | Schmelzeisen-Redeker et al. |
| 2005/0148003 A1* | 7/2005 | Keith ............... G01N 21/6428 435/7.1 |
| 2011/0081726 A1* | 4/2011 | Berman ............. A61B 5/14532 436/95 |
| 2013/0241745 A1 | 9/2013 | Colvin, Jr. et al. |
| 2014/0005505 A1 | 1/2014 | Peyser et al. |
| 2015/0045635 A1* | 2/2015 | Tankiewicz ........ A61B 5/14503 600/309 |
| 2015/0164384 A1* | 6/2015 | Varsavsky .......... G01N 27/3274 600/316 |
| 2017/0215805 A1 | 8/2017 | Goode et al. |
| 2018/0103879 A1 | 4/2018 | Masciotti et al. |

FOREIGN PATENT DOCUMENTS

| | | |
|---|---|---|
| EP | 2329770 B1 | 9/2014 |
| EP | 1942801 B1 | 10/2018 |
| WO | 03/094714 A1 | 11/2003 |

\* cited by examiner

ASSESSMENT OF PERFORMANCE OF AN IMPLANTED SENSOR

CROSS-REFERENCE TO RELATED APPLICATION

The present application is a divisional of U.S. application Ser. No. 16/709,225, filed on Dec. 10, 2019, which claims the benefit of priority to U.S. Provisional Application Ser. No. 62/777,591, filed on Dec. 10, 2018, which are incorporated herein by reference in their entireties.

BACKGROUND

Field of Invention

Aspects of the present invention relate to analyte monitoring, assessing in real time sensor performance, and determining whether sensor performance is no longer suitable for analyte monitoring.

Discussion of the Background

The prevalence of diabetes mellitus continues to increase in industrialized countries, and projections suggest that this figure will rise to 4.4% of the global population (366 million individuals) by the year 2030. Glycemic control is a key determinant of long-term outcomes in patients with diabetes, and poor glycemic control is associated with retinopathy, nephropathy and an increased risk of myocardial infarction, cerebrovascular accident, and peripheral vascular disease requiring limb amputation. Despite the development of new insulins and other classes of antidiabetic therapy, roughly half of all patients with diabetes do not achieve recommended target hemoglobin A1c (HbA1c) levels <7.0%.

Frequent self-monitoring of blood glucose (SMBG) is necessary to achieve tight glycemic control in patients with diabetes mellitus, particularly for those requiring insulin therapy. However, current blood (finger-stick) glucose tests are burdensome, and, even in structured clinical studies, patient adherence to the recommended frequency of SMBG decreases substantially over time. Moreover, finger-stick measurements only provide information about a single point in time and do not yield information regarding intraday fluctuations in blood glucose levels that may more closely correlate with some clinical outcomes.

Continuous glucose monitors (CGMs) have been developed in an effort to overcome the limitations of finger-stick SMBG and thereby help improve patient outcomes. These systems enable increased frequency of glucose measurements and a better characterization of dynamic glucose fluctuations, including episodes of unrealized hypoglycemia. Furthermore, integration of CGMs with automated insulin pumps allows for establishment of a closed-loop "artificial pancreas" system to more closely approximate physiologic insulin delivery and to improve adherence.

Monitoring real-time analyte measurements from a living body via wireless analyte monitoring sensor(s) may provide numerous health and research benefits. There is a need to enhance such analyte monitoring systems via innovations comprising, but not limited to, the ability to assess the performance of an analyte sensor in an analyte monitoring system.

SUMMARY

One aspect of the invention may provide an analyte monitoring system including an analyte sensor and a transceiver. The analyte sensor may include an indicator that exhibits one or more detectable properties based on an amount or concentration of an analyte in a first medium in proximity to the indicator. The transceiver may be configured to (i) receive one or more sensor measurements from the analyte sensor, (ii) assess a performance of the analyte sensor based on at least one or more of the received one or more sensor measurements, (iii) determine whether the performance of the analyte sensor is deficient based at least on the assessed performance of the analyte sensor, and (iv) if the performance of the analyte sensor is determined to be deficient, display a sensor retirement indication.

In some aspects, the analyte monitoring system may further include a display device, the transceiver may be configured to display the sensor retirement indication by conveying a sensor retirement communication to the display device, and the display device may be configured to receive the sensor retirement communication and, in response to receiving the sensor retirement communication, display an indication that the analyte sensor needs to be replaced.

In some aspects, the transceiver may be further configured to calculate an analyte level using at least one or more of the received one or more sensor measurements and, only if the performance of the analyte sensor is not determined to be deficient, display the calculated analyte level. In some aspects, the transceiver may further include a display device, the transceiver may be configured to display the calculated analyte level by conveying the calculated analyte level to the display device, and the display device may be configured to receive and display the calculated analyte level. In some aspects, the calculated analyte level may be a calculation of an amount or concentration of the analyte in a second medium ("second medium analyte level"). In some aspects, the transceiver may be configured to calculate an amount or concentration of the analyte in the first medium ("first medium analyte level") using at least one or more of the received one or more sensor measurements. In some aspects, the transceiver may be configured to calculate a rate of change of the amount or concentration of the analyte in the first medium ("first medium analyte level rate of change") using at least the calculated first medium analyte level and one or more previous first medium analyte levels. In some aspects, the transceiver may be configured to calculate the second medium analyte level using at least the first medium analyte level and the first medium analyte level rate of change.

In some aspects, assessing the performance of the analyte sensor may include calculating one or more of a spike metric, a reference channel instability metric, a diagnostic drift metric, and a reference channel decrease metric. In some aspects, assessing the performance of the analyte sensor may include calculating the minimum of two or more of a spike metric, a reference channel instability metric, a diagnostic drift metric, and a reference channel decrease metric. In some aspects, one or more of the spike metric, the reference channel instability metric, the diagnostic drift metric, and the reference channel decrease metric may be weighted.

In some aspects, determining whether the performance of the analyte sensor is deficient may include comparing the assessed performance of the analyte sensor to a deficiency threshold. In some aspects, determining whether the performance of the analyte sensor is deficient may include determining whether the assessed performance is below a deficiency threshold for at least a period of time.

Another aspect of the invention may provide a method including receiving one or more sensor measurements from an analyte sensor, and the analyte sensor may include an indicator that exhibits one or more detectable properties based on an amount or concentration of an analyte in a first medium in proximity to the indicator. The method may include assessing a performance of the analyte sensor based on at least one or more of the received one or more sensor measurements. The method may include determining that the performance of the analyte sensor is deficient based on at least the assessed performance of the analyte sensor. The method may include, as a result of determining that the performance of the analyte sensor is deficient, displaying a sensor retirement indication.

In some aspects, displaying the sensor retirement indication may include conveying a sensor retirement communication to a display device, and the method may further include using the display device to receive the sensor retirement communication and, in response to receiving the sensor retirement communication, displaying an indication that the analyte sensor needs to be replaced.

Still another aspect of the invention may provide a method including using a sensor interface of a transceiver to receive one or more first sensor measurements from an analyte sensor, and the analyte sensor may include an indicator that exhibits one or more detectable properties based on an amount or concentration of an analyte in a first medium in proximity to the indicator. The method may include using a processor of the transceiver to calculate a first analyte level using at least one or more of the received one or more first sensor measurements. The method may include using the processor of the transceiver to perform a first assessment of a performance of the analyte sensor based on at least one or more of the received one or more first sensor measurements. The method may include using the processor of the transceiver to determine that the performance of the analyte sensor is not deficient based on at least the first assessment of the performance of the analyte sensor. The method may include, as a result of determining that the performance of the analyte sensor is not deficient, displaying the calculated first analyte level. The method may include using the sensor interface of the transceiver to receive one or more second sensor measurements from the analyte sensor. The method may include using the processor of the transceiver to calculate a second analyte level using at least one or more of the received one or more second sensor measurements. The method may include using the processor of the transceiver to perform a second assessment of the performance of the analyte sensor based on at least one or more of the received one or more second sensor measurements. The method may include using the processor of the transceiver to determine that the performance of the analyte sensor is deficient based on at least the second assessment of the performance of the analyte sensor. The method may include, as a result of determining that the performance of the analyte sensor is deficient, displaying a sensor retirement indication and not displaying the second analyte level.

In some aspects, displaying the calculated first analyte level may include conveying the calculated first analyte level to a display device, and displaying the sensor retirement indication may include conveying a sensor retirement communication to a display device. In some aspects, the method may further include using the display device to: receive and display the calculated first analyte level, receive the sensor retirement communication, and, in response to receiving the sensor retirement communication, display an indication that the analyte sensor needs to be replaced. In some aspects, the calculated first analyte level may be a calculation of an amount or concentration of the analyte in a second medium ("second medium analyte level"). In some aspects, calculating the second medium analyte level may include calculating an amount or concentration of the analyte in the first medium ("first medium analyte level") using at least one or more of the received one or more sensor measurements. In some aspects, calculating the second medium analyte level may include calculating a rate of change of the amount or concentration of the analyte in the first medium ("first medium analyte level rate of change") using at least the calculated first medium analyte level and one or more previous first medium analyte levels. In some aspects, calculating the second medium analyte level may include calculating the second medium analyte level using at least the first medium analyte level and the first medium analyte level rate of change.

In some aspects, assessing the performance of the analyte sensor may include calculating one or more of a spike metric, a reference channel instability metric, a diagnostic drift metric, and a reference channel decrease metric. In some aspects, assessing the performance of the analyte sensor may include calculating the minimum of two or more of a spike metric, a reference channel instability metric, a diagnostic drift metric, and a reference channel decrease metric. In some aspects, one or more of the spike metric, the reference channel instability metric, the diagnostic drift metric, and the reference channel decrease metric may be weighted.

In some aspects, determining whether the performance of the analyte sensor is deficient may include comparing the assessed performance of the analyte sensor to a deficiency threshold. In some aspects, determining whether the performance of the analyte sensor is deficient may include determining whether the assessed performance is below a deficiency threshold for at least a period of time. In some aspects, the method may further include performing a spike analysis on the calculated first analyte level. In some aspects, the method may further include performing a reference channel instability analysis using at least one or more received sensor measurements.

Yet another aspect of the invention may provide an analyte monitoring system including an analyte sensor and a transceiver. The analyte sensor may include an indicator that exhibits one or more detectable properties based on an amount or concentration of an analyte in a first medium in proximity to the indicator. The transceiver may be configured to receive one or more first sensor measurements from the analyte sensor. The transceiver may be configured to calculate a first analyte level using at least one or more of the received one or more first sensor measurements. The transceiver may be configured to receive one or more second sensor measurements from the analyte sensor. The transceiver may be configured to calculate a second analyte level using at least one or more of the received one or more second sensor measurements. The transceiver may be configured to perform a spike analysis to determine whether the second analyte level is a spike. The transceiver may be configured to, if the second analyte level is not determined to be a spike, display the second analyte level. The transceiver may be configured to, if the second analyte level is determined to be a spike, calculate and display an alternative second analyte level.

In some aspects, the analyte monitoring system may further include a display device, the transceiver may be configured to display the second analyte level by conveying the second analyte level to the display device, the display device may be configured to receive and display the second analyte level, the transceiver may be configured to display the alternative second analyte level by conveying the alternative second analyte level to the display device, and the display device may be configured to receive and display the alternative second analyte level. In some aspects, the spike analysis may include calculating an analyte level rate of change and comparing an absolute value of the analyte level rate of change to a rate of change threshold. In some aspects, the analyte level rate of change may be calculated as equal to the difference between the first and second analyte levels divided by the difference between time stamps for the first and second analyte levels.

In some aspects, the spike analysis may include calculating a first analyte level rate of change for the first analyte level, calculating a second analyte level rate of change for the second analyte level, and comparing an absolute value of the difference between the first and second analyte level rates of change to a rate of change difference threshold. In some aspects, calculating the alternative second analyte level may include calculating one or more of (i) a predicted second analyte level using at least the first analyte level and a first analyte level rate of change for the first analyte level, (ii) a threshold-limited second analyte level using at least the first analyte level and a rate of change threshold, and (iii) a dynamic Kalman filtered second analyte value. In some aspects, calculating the alternative second analyte level may include calculating two or more of (i) a predicted second analyte level using at least the first analyte level and a first analyte level rate of change for the first analyte level, (ii) a threshold-limited second analyte level using at least the first analyte level and a rate of change threshold, and (iii) a dynamic Kalman filtered second analyte value. In some aspects, calculating the alternative second analyte level may include calculating an average of two or more of (i) a predicted second analyte level calculated using at least the first analyte level and a first analyte level rate of change for the first analyte level, (ii) a threshold-limited second analyte level calculated using at least the first analyte level and a rate of change threshold, and (iii) a dynamic Kalman filtered second analyte value.

In some aspects, the transceiver may be further configured to: perform a spike analysis to determine whether the first analyte level is a spike, and, if the first analyte level was determined to be a spike, use at least the second analyte level to determine whether the first analyte level truly was a spike. In some aspects, the first analyte level may be a calculation of an amount or concentration of the analyte in a second medium ("first M2_AL"), and the second analyte level may be a calculation of an amount or concentration of the analyte in the second medium ("second M2_AL"). In some aspects, the transceiver may be configured to calculate a first amount or concentration of the analyte in the first medium ("first M1_AL") using at least one or more of the received one or more first sensor measurements. In some aspects, the transceiver may be configured to calculate a first rate of change of the amount or concentration of the analyte in the first medium ("first M1_ROC") using at least the calculated first M1_AL and one or more previous M1_ALs. In some aspects, the transceiver may be configured to calculate the first M2_AL using at least the first M1_AL and the first M1_ROC. In some aspects, the transceiver may be configured to calculate a second amount or concentration of the analyte in the first medium ("second M1_AL") using at least one or more of the received one or more second sensor measurements. In some aspects, the transceiver may be configured to calculate a second rate of change of the amount or concentration of the analyte in the first medium ("second M1_ROC") using at least the calculated second M1_AL and the calculated first M1_AL. In some aspects, the transceiver may be configured to calculate the second M2_AL using at least the second M1_AL and the second M1_ROC. In some aspects, the spike analysis to determine whether the second analyte level is a spike may include comparing an absolute value of the second M1_ROC to a rate of change threshold. In some aspects, the second M1_ROC may be calculated as equal to the difference between the second M1_AL and the first M1_AL divided by the difference between a time stamp for the second M1_AL and a time stamp for the first M1_AL. In some aspects, the spike analysis to determine whether the second analyte level is a spike may include comparing an absolute value of the difference between the first M1_ROC and the second M1_ROC to a rate of change difference threshold.

Yet another aspect of the invention may provide a method including using a sensor interface of a transceiver to receive one or more first sensor measurements from an analyte sensor, and the analyte sensor may include an indicator that exhibits one or more detectable properties based on an amount or concentration of an analyte in a first medium in proximity to the indicator. The method may include using a processor of the transceiver to calculate a first analyte level using at least one or more of the received one or more first sensor measurements. The method may include using the processor of the transceiver to perform a spike analysis and determine that the first analyte level is not a spike. The method may include using the processor of the transceiver to convey the first analyte level to a display device. The method may include using the processor of the transceiver to receive one or more second sensor measurements from the analyte sensor. The method may include using the processor of the transceiver to calculate a second analyte level using at least one or more of the received one or more second sensor measurements. The method may include using the processor of the transceiver to perform a spike analysis and determine that the second analyte level is a spike. The method may include using the processor of the transceiver to calculate an alternative second analyte level. The method may include using the transceiver to convey the alternative second analyte level to the display device.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting aspects of the present invention. In the drawings, like reference numbers indicate identical or functionally similar elements.

DETAILED DESCRIPTION OF PREFERRED EMBODIMENTS

Figure 1:
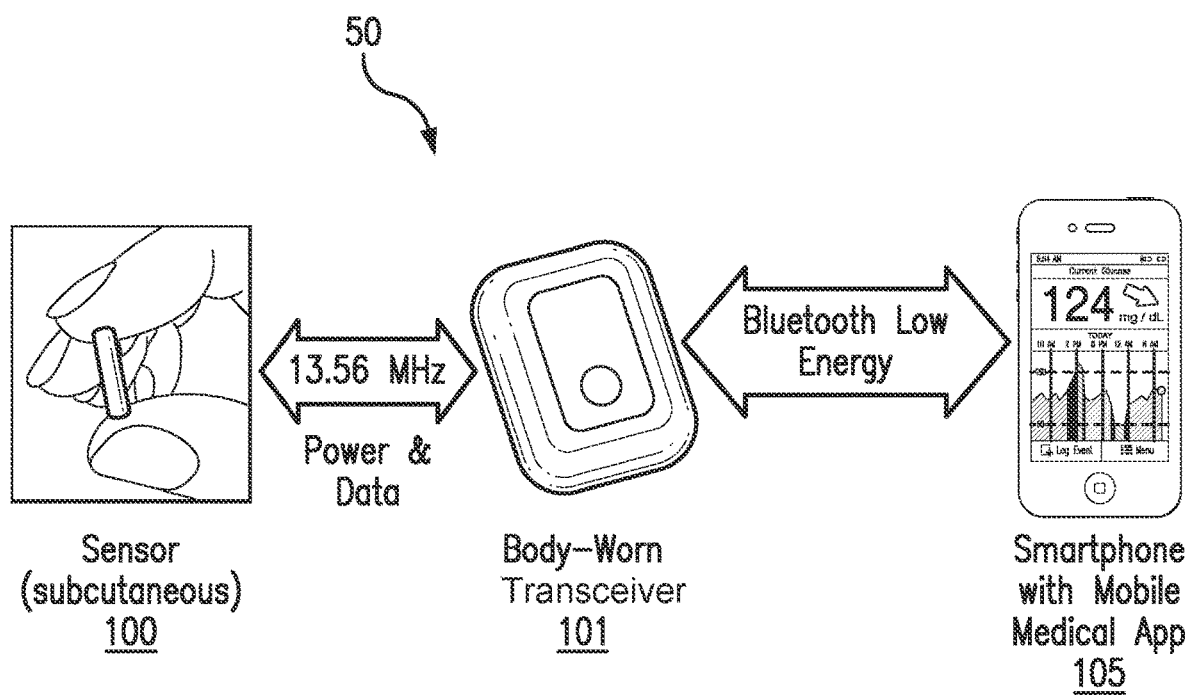
FIG. 1 is a schematic view illustrating an analyte monitoring system embodying aspects of the present invention.

FIG. 1 is a schematic view of an exemplary analyte monitoring system 50 embodying aspects of the present invention. The analyte monitoring system 50 may be a continuous analyte monitoring system (e.g., a continuous glucose monitoring system). In some aspects, the analyte monitoring system 50 may include one or more of an analyte sensor 100, a transceiver 101, and a display device 105. In some aspects, the sensor 100 may be a small, fully subcutaneously implantable sensor that takes one or more measurements indicative of analyte (e.g., glucose) levels in a first medium (e.g., interstitial fluid) of a living animal (e.g., a living human). However, this is not required, and, in some alternative aspects, the sensor 100 may be a partially implantable (e.g., transcutaneous) sensor or a fully external sensor.

In some aspects, the transceiver 101 may be an externally worn transceiver (e.g., attached via an armband, wristband, waistband, or adhesive patch). In some aspects, the transceiver 101 may remotely power and/or communicate with the sensor to initiate and receive the measurements (e.g., via near field communication (NFC)). However, this is not required, and, in some alternative aspects, the transceiver 101 may power and/or communicate with the sensor 100 via one or more wired connections. In some non-limiting aspects, the transceiver 101 may be a smartphone (e.g., an NFC-enabled smartphone). In some aspects, the transceiver 101 may communicate information (e.g., one or more analyte levels) wirelessly (e.g., via a Bluetooth™ communication standard such as, for example and without limitation Bluetooth Low Energy) to a hand held application running on a display device 105 (e.g., smartphone). In some aspects, information can be downloaded from the transceiver 101 through a Universal Serial Bus (USB) port. In some aspects, the analyte monitoring system 50 may include a web interface for plotting and sharing of uploaded data.

Figure 2:
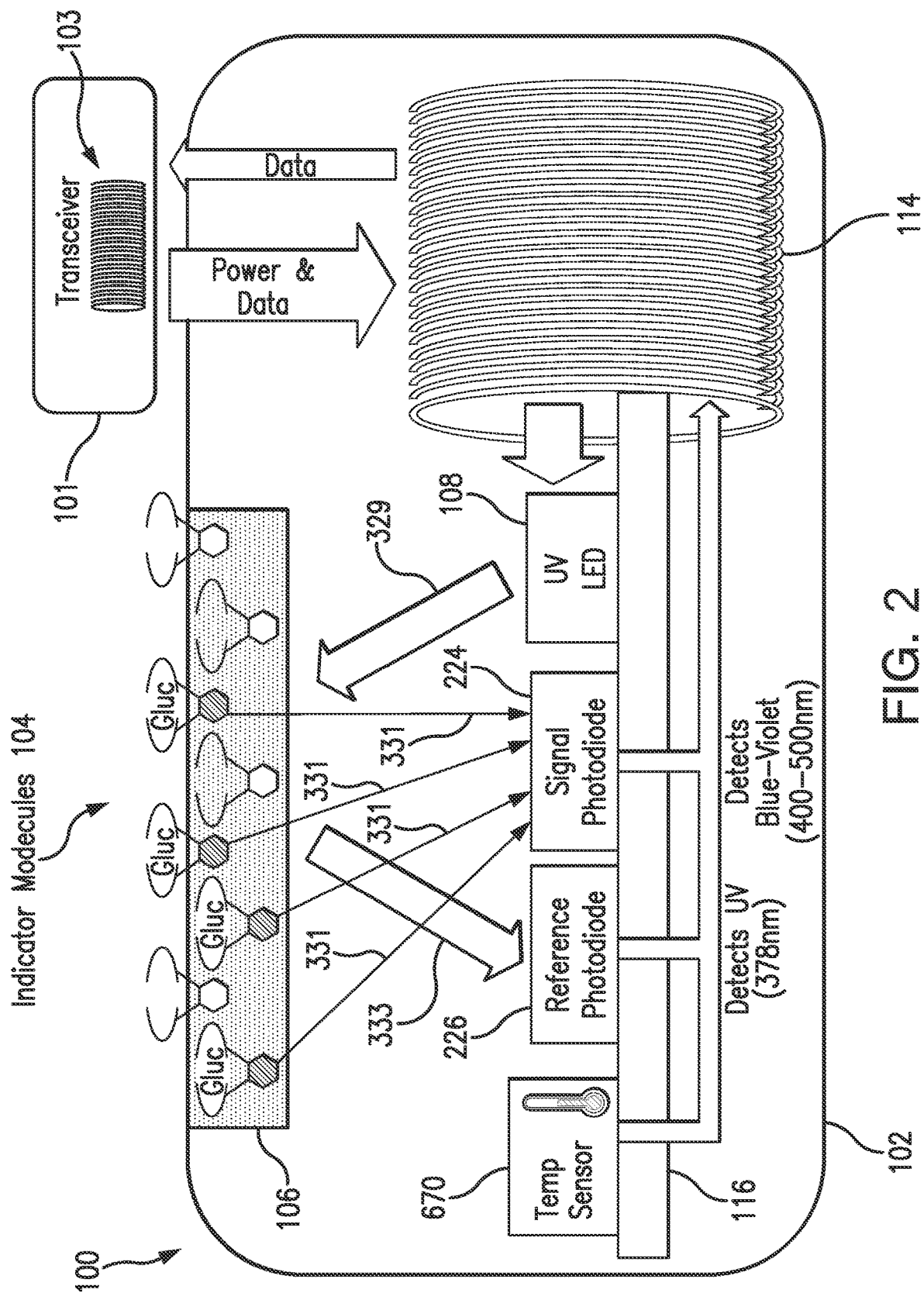
FIG. 2 is a schematic view illustrating a sensor and transceiver of an analyte monitoring system embodying aspects of the present invention.

In some aspects, as illustrated in FIG. 2, the transceiver 101 may include an inductive element 103, such as, for example, a coil. In some aspects, the transceiver 101 may generate an electromagnetic wave or electrodynamic field (e.g., by using a coil) to induce a current in an inductive element 114 of the sensor 100. In some non-limiting aspects, the sensor 100 may use the current induced in the inductive element 114 to power the sensor 100. However, this is not required, and, in some alternative aspects, the sensor 100 may be powered by an internal power source (e.g., a battery).

In some aspects, the transceiver 101 may convey data (e.g., commands) to the sensor 100. For example, in some non-limiting aspects, the transceiver 101 may convey data by modulating the electromagnetic wave generated by the inductive element 103 (e.g., by modulating the current flowing through the inductive element 103 of the transceiver 101). In some aspects, the sensor 100 may detect/extract the modulation in the electromagnetic wave generated by the transceiver 101. Moreover, the transceiver 101 may receive data (e.g., one or more sensor measurements) from the sensor 100. For example, in some non-limiting aspects, the transceiver 101 may receive data by detecting modulations in the electromagnetic wave generated by the sensor 100, e.g., by detecting modulations in the current flowing through the inductive element 103 of the transceiver 101.

In some non-limiting aspects, as illustrated in FIG. 2, the sensor 100 may be include a sensor housing 102 (i.e., body, shell, capsule, or encasement), which may be rigid and biocompatible. The sensor 100 may include an analyte indicator 106, such as, for example, a polymer graft coated, diffused, adhered, or embedded on or in at least a portion of the exterior surface of the sensor housing 102. The analyte indicator 106 (e.g., polymer graft) of the sensor 100 may include indicator molecules 104 (e.g., fluorescent indicator molecules) exhibiting one or more detectable properties (e.g., optical properties) based on the level, amount, or concentration of the analyte in proximity to the analyte indicator 106.

In some aspects, as shown in FIG. 2, the sensor 100 may include a light source 108 that emits excitation light 329 over a range of wavelengths that interact with the indicator molecules 104. The sensor 100 may also include one or more photodetectors 224, 226 (e.g., photodiodes, phototransistors, photoresistors, or other photosensitive elements). The one or more photodetectors (e.g., photodetector 224) may be sensitive to emission light 331 (e.g., fluorescent light) emitted by the indicator molecules 104 such that a signal generated by a photodetector (e.g., photodetector 224) in response thereto that is indicative of the level of emission light 331 of the indicator molecules and, thus, the amount of analyte of interest (e.g., glucose). In some non-limiting aspects, one or more of the photodetectors (e.g., photodetector 226) may be sensitive to excitation light 329 that is reflected from the analyte indicator 106 as reflection light 333. In some non-limiting aspects, one or more of the photodetectors may be covered by one or more filters (e.g., one or more bandpass filters) that allow only a certain subset of wavelengths of light to pass through (e.g., a subset of wavelengths corresponding to emission light 331 or a subset of wavelengths corresponding to reflection light 333) and reflect the remaining wavelengths. In some non-limiting aspects, the sensor 100 may include a temperature transducer 670.

In some aspects, as illustrated in FIG. 2, the sensor 100 may include a substrate 116. In some aspects, the substrate 116 may be a circuit board (e.g., a printed circuit board (PCB) or flexible PCB) on which circuit components (e.g., analog and/or digital circuit components) may be mounted or otherwise attached. However, in some alternative aspects, the substrate 116 may be a semiconductor substrate having circuitry fabricated therein. The circuitry may include analog and/or digital circuitry. Also, in some semiconductor substrate aspects, in addition to the circuitry fabricated in the semiconductor substrate, circuitry may be mounted or otherwise attached to the semiconductor substrate 116. In other words, in some semiconductor substrate aspects, a portion or all of the circuitry, which may include discrete circuit elements, an integrated circuit (e.g., an application specific integrated circuit (ASIC)) and/or other electronic components (e.g., a non-volatile memory), may be fabricated in the semiconductor substrate 116 with the remainder of the circuitry is secured to the semiconductor substrate 116 and/or a core (e.g., ferrite core) for the inductive element 114. In some aspects, the semiconductor substrate 116 and/or a core may provide communication paths between the various secured components.

In some aspects, the one or more of the sensor housing 102, analyte indicator 106, indicator molecules 104, light source 108, photodetectors 224, 226, temperature transducer 670, substrate 116, and inductive element 114 of sensor 100 may include some or all of the features described in one or more of U.S. patent application Ser. No. 13/761,839, filed on Feb. 7, 2013, U.S. patent application Ser. No. 13/937,871, filed on Jul. 9, 2013, and U.S. patent application Ser. No. 13/650,016, filed on Oct. 11, 2012, all of which are incorporated by reference in their entireties. Similarly, the structure and/or function of the sensor 100 and/or transceiver 101 may be as described in one or more of U.S. patent application Ser. Nos. 13/761,839, 13/937,871, and 13/650,016.

Although in some aspects, as illustrated in FIG. 2, the sensor 100 may be an optical sensor, this is not required, and, in one or more alternative aspects, sensor 100 may be a different type of analyte sensor, such as, for example, an electrochemical sensor, a diffusion sensor, or a pressure sensor. Also, although in some aspects, as illustrated in FIGS. 1 and 2, the analyte sensor 100 may be a fully implantable sensor, this is not required. In some alternative aspects, the sensor 100 may be a transcutaneous sensor having a wired connection to the transceiver 101. For example, in some alternative aspects, the sensor 100 may be located in or on a transcutaneous needle (e.g., at the tip thereof). In these aspects, instead of wirelessly communicating using inductive elements 103 and 114, the sensor 100 and transceiver 101 may communicate using one or more wires connected between the transceiver 101 and the transceiver transcutaneous needle that includes the sensor 100. For another example, in some alternative aspects, the sensor 100 may be located in a catheter (e.g., for intravenous blood glucose monitoring) and may communicate (wirelessly or using wires) with the transceiver 101.

In some aspects, the sensor 100 may include a transceiver interface device. In some aspects where the sensor 100 includes an antenna (e.g., inductive element 114), the transceiver interface device may include the antenna (e.g., inductive element 114) of sensor 100. In some of the transcutaneous aspects where there exists a wired connection between the sensor 100 and the transceiver 101, the transceiver interface device may include the wired connection.

Figure 3:
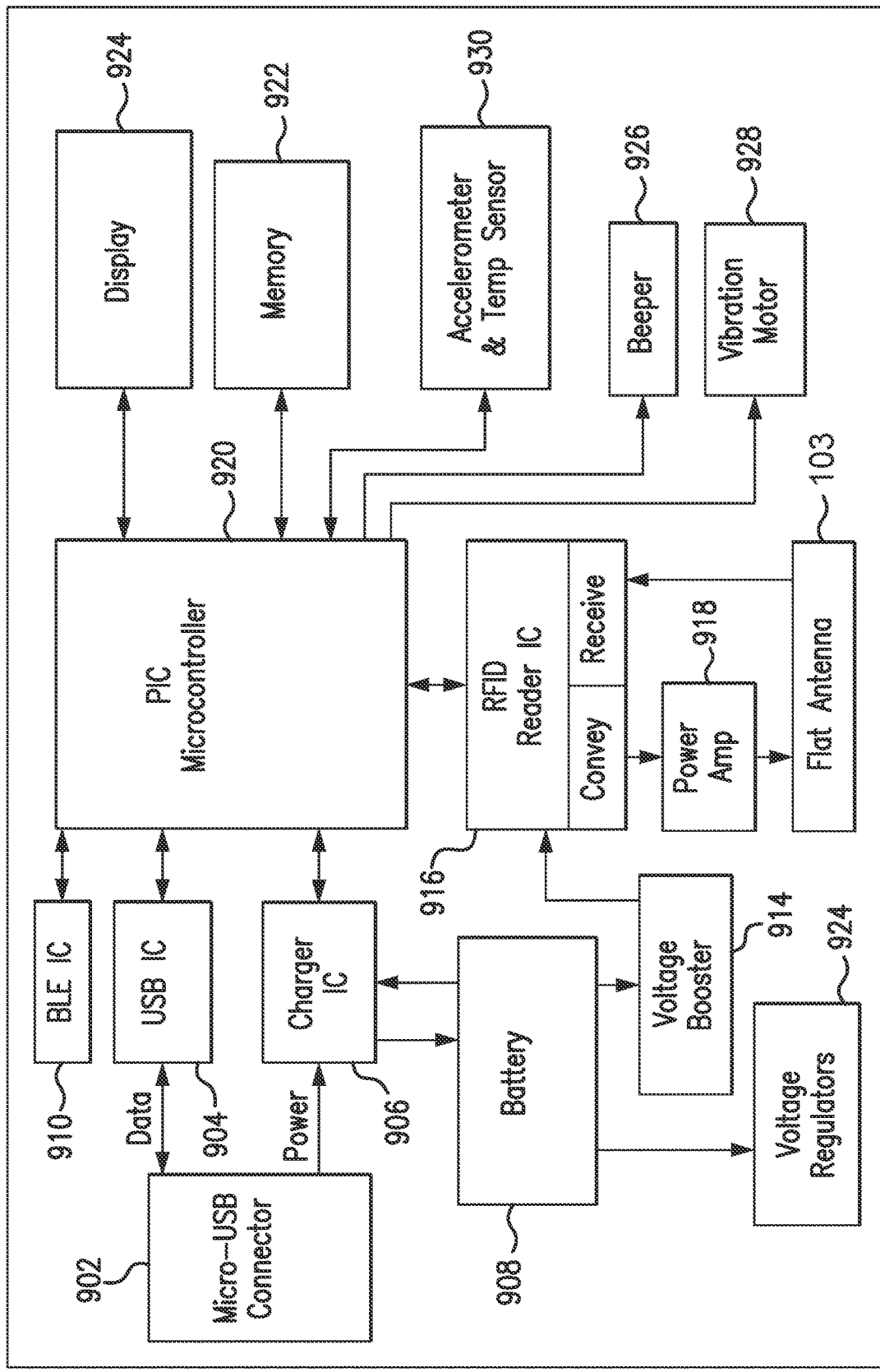
FIG. 3 is a schematic view illustrating a transceiver embodying aspects of the present invention.

FIG. 3 is a schematic view of an external transceiver 101 according to a non-limiting embodiment. In some aspects, as shown in FIG. 3, the transceiver 101 may have a connector 902, such as, for example, a Micro-Universal Serial Bus (USB) connector. The connector 902 may enable a wired connection to an external device, such as a personal computer (e.g., personal computer 109) or a display device 105 (e.g., a smartphone).

The transceiver 101 may exchange data to and from the external device through the connector 902 and/or may receive power through the connector 902. The transceiver 101 may include a connector integrated circuit (IC) 904, such as, for example, a USB-IC, which may control transmission and receipt of data through the connector 902. The transceiver 101 may also include a charger IC 906, which may receive power via the connector 902 and charge a battery 908 (e.g., lithium-polymer battery). In some aspects, the battery 908 may be rechargeable, may have a short recharge duration, and/or may have a small size.

In some aspects, the transceiver 101 may include one or more connectors in addition to (or as an alternative to) Micro-USB connector 904. For example, in one alternative embodiment, the transceiver 101 may include a spring-based connector (e.g., Pogo pin connector) in addition to (or as an alternative to) Micro-USB connector 904, and the transceiver 101 may use a connection established via the spring-based connector for wired communication to a personal computer (e.g., personal computer 109) or a display device 105 (e.g., a smartphone) and/or to receive power, which may be used, for example, to charge the battery 908.

In some aspects, as shown in FIG. 3, the transceiver 101 may have a wireless communication IC 910, which enables wireless communication with an external device, such as, for example, one or more personal computers (e.g., personal computer 109) or one or more display devices 105 (e.g., a smartphone). In one non-limiting embodiment, the wireless communication IC 910 may employ one or more wireless communication standards to wirelessly transmit data. The wireless communication standard employed may be any suitable wireless communication standard, such as an ANT standard, a Bluetooth standard, or a Bluetooth Low Energy (BLE) standard (e.g., BLE 4.0). In some non-limiting aspects, the wireless communication IC 910 may be configured to wirelessly transmit data at a frequency greater than 1 gigahertz (e.g., 2.4 or 5 GHz). In some aspects, the wireless communication IC 910 may include an antenna (e.g., a Bluetooth antenna). In some non-limiting aspects, the antenna of the wireless communication IC 910 may be entirely contained within the housing (e.g., housing 206 and 220) of the transceiver 101. However, this is not required, and, in alternative aspects, all or a portion of the antenna of the wireless communication IC 910 may be external to the transceiver housing.

In some aspects, the transceiver 101 may include a display interface device, which may enable communication by the transceiver 101 with one or more display devices 105. In some aspects, the display interface device may include the antenna of the wireless communication IC 910 and/or the connector 902. In some non-limiting aspects, the display interface device may additionally include the wireless communication IC 910 and/or the connector IC 904.

In some aspects, as shown in FIG. 3, the transceiver 101 may include voltage regulators 912 and/or a voltage booster 914. The battery 908 may supply power (via voltage booster 914) to radio-frequency identification (RFID) reader IC 916, which uses the inductive element 103 to convey information (e.g., commands) to the sensor 101 and receive information (e.g., measurement information) from the sensor 100. In some non-limiting aspects, the sensor 100 and transceiver 101 may communicate using near field communication (NFC) (e.g., at a frequency of 13.56 MHz). In the illustrated embodiment, the inductive element 103 is a flat antenna. In some non-limiting aspects, the antenna may be flexible. However, the inductive element 103 of the transceiver 101 may be in any configuration that permits adequate field strength to be achieved when brought within adequate physical proximity to the inductive element 114 of the sensor 100. In some aspects, the transceiver 101 may include a power amplifier 918 to amplify the signal to be conveyed by the inductive element 103 to the sensor 100.

In some aspects, as shown in FIG. 3, the transceiver 101 may include a processor 920 and a memory 922 (e.g., Flash memory). In some non-limiting aspects, the memory 922 may be non-volatile and/or capable of being electronically erased and/or rewritten. In some non-limiting aspects, the processor 920 may be, for example and without limitation, a peripheral interface controller (PIC) microcontroller. In some aspects, the processor 920 may control the overall operation of the transceiver 101. For example, the processor 920 may control the connector IC 904 or wireless communication IC 910 to transmit data via wired or wireless communication and/or control the RFID reader IC 916 to convey data via the inductive element 103. The processor 920 may also control processing of data received via one or more of the inductive element 103, connector 902, and wireless communication IC 910.

In some aspects, the transceiver 101 may include a sensor interface device, which may enable communication by the transceiver 101 with a sensor 100. In some aspects, the sensor interface device may include the inductive element 103. In some non-limiting aspects, the sensor interface device may additionally include the RFID reader IC 916 and/or the power amplifier 918. However, in some alternative aspects where there exists a wired connection between the sensor 100 and the transceiver 101 (e.g., transcutaneous aspects), the sensor interface device may include the wired connection.

In some aspects, as shown in FIG. 3, the transceiver 101 may include a display 924 (e.g., liquid crystal display and/or one or more light emitting diodes), which processor 920 may control to display data (e.g., analyte levels). In some aspects, the transceiver 101 may include a speaker 926 (e.g., a beeper) and/or a vibration motor 928, which may be activated, for example, in the event that an alarm condition (e.g., detection of a hypoglycemic or hyperglycemic condition) is met. The transceiver 101 may also include one or more additional sensors 930, which may include an accelerometer and/or a temperature sensor, that may be used in the processing performed by the processor 920.

In some aspects, the transceiver 101 may be a body-worn transceiver that is a rechargeable, external device worn over the sensor implantation or insertion site. In some aspects, the transceiver 101 may be placed using an adhesive patch or a specially designed strap or belt. In some non-limiting aspects, the transceiver 101 may supply power to the proximate sensor 100. In some non-limiting aspects, power may be supplied to the sensor 100 through an inductive link (e.g., an inductive link of 13.56 MHz). However, it is not required that the sensor 100 receive power from the transceiver 101 (e.g., in the case of a battery-powered sensor).

In some aspects, the external transceiver 101 may receive from the analyte sensor 100 one or more sensor measurements indicative of an analyte level in a first medium (e.g., interstitial fluid) in proximity to the analyte indicator 106 of the analyte sensor 100. In some non-limiting aspects, the one or more sensor measurements may include, for example and without limitation, light and/or temperature measurements (e.g., one or more measurements indicative of the level of emission light 331 from the indicator molecules 104 as measured by the photodetector 224, one or more measurements indicative of the level of reflection light 333 as measured by the photodetector 226, and/or one or more temperature measurements as measured by the temperature transducer 670). In some non-limiting aspects, the transceiver 101 may receive one or more sensor measurements periodically (e.g., every 1, 2, 5, 10, or 15 minutes). However, this is not required, and, in some alternative aspects, the transceiver 101 may receive one or more sensor measurements (e.g., by swiping, hovering, or otherwise bringing the transceiver 101 in proximity to the sensor 101).

In some aspects, the transceiver 101 may calculate a level (e.g., concentration) of the analyte (e.g., glucose) in the first medium using at least the received one or more sensor measurements. In some aspects, the transceiver 101 may additionally or alternatively calculate a level of the analyte in a second medium (e.g., blood) using at least the received one or more sensor measurements and/or the calculated first medium analyte level. In some non-limiting aspects, the transceiver 101 may calculate the second medium analyte level as $M1\_ROC/p_2+(1+p_3/p_2)*M1$ analyte, where M1_ROC is the rate of change of the first medium analyte level, $p_2$ is analyte diffusion rate, $p_3$ is the analyte consumption rate, and M1 analyte is the calculated first medium analyte level. In some aspects, the transceiver 101 may display one or more calculated analyte levels (e.g., one or calculated second medium analyte levels) by displaying the analyte levels on a display of the transceiver 101 or conveying the analyte levels to a display device 105 (see FIG. 1). In some aspects, the transceiver 101 may calculate one or more analyte level trends. In some aspects, the transceiver 101 may determine whether an alert and/or alarm condition exists, which may be signaled to the user (e.g., through vibration by vibration motor 928 and/or an LED of the transceiver's display 924 and/or a user interface of a display device 105). In some aspects, the transceiver 101 may store one or more calculated analyte levels (e.g., in memory 922).

In some aspects, the transceiver 101 may convey information (e.g., one or more of sensor data, calculated analyte levels, calculated analyte level rates of change, alerts, alarms, and notifications) may be transmitted to a display device 105 (e.g., via Bluetooth Low Energy with Advanced Encryption Standard (AES)-Counter CBC-MAC (CCM) encryption) for display by a mobile medical application (MMA) being executed by the display device 105. In some non-limiting aspects, the MMA may generate alarms, alerts, and/or notifications (in addition to or as an alternative to receiving alerts, alarms, and/or notifications from the transceiver 101). In one embodiment, the MMA may be configured to provide push notifications.

In some aspects, the analyte monitoring system 50 may calibrate the conversion of one or more sensor measurements to one or more analyte levels. In some aspects, the calibration may be performed approximately periodically (e.g., every 12 or 24 hours). In some aspects, the calibration may be performed using one or more reference measurements (e.g., one or more self-monitoring blood glucose (SMBG) measurements), which may be entered into the analyte monitoring system 50 using the user interface of the display device 105. In some aspects, the transceiver 101 may receive the one or more reference measurements from the display device 105 and perform the calibration using the one or more reference measurements as calibration points.

In some aspects, the analyte monitoring system 50 may assess the performance of the analyte sensor 100. In some aspects, circuitry of the transceiver 101 (e.g., the processor 920) may perform the assessment of the performance of the analyte sensor 100. In some aspects, the assessment of the electronic performance may provide an objective reference to quantify the overall sensor electronic performance. In some aspects, the assessment of the sensor electronic performance may be performed in real time. In some aspects, the transceiver 101 may assess the in-vivo sensor performance in real time and determine whether the performance of the analyte sensor 100 is suitable for continuous analyte monitoring. In some aspects, the analyte monitoring system 50 may trigger one or more of a sensor instability alert and a sensor retirement alert if the sensor electronic performance is unsuitable for continuous analyte monitoring.

In some aspects, the analyte monitoring system 50 may assess the performance of the analyte sensor 100 at each sensor measurement. In some aspects, assessing the performance of the analyte sensor 100 may include calculating a metric for electronic performance (MEP). In some aspects, the MEP may reflect the real time sensor electronic performance and may be used to determine a sensor electronic performance deficiency and/or to trigger a sensor retirement alert. In some aspects, the MEP may take into account measures of one or more of spikes in the calculated analyte levels, reference channel instability, diagnostic drift, and reference channel decreases.

In some aspects, the MEP may be the minimum value of one or more measures. In some aspects, the measures may include one or more of (i) a spike metric, (ii) a reference channel instability metric, (iii) a diagnostic drift metric, and (iv) a reference channel decrease metric, which are described in detail below. In some aspects, the MEP may be the minimum value of one or more measures after applying a weight to one or more of the measures. In some non-limiting aspects, MEP may be defined as the minimum value of (i) a weighted spike metric, (ii) a weighted reference channel instability metric, (iii) a weighted diagnostic drift metric, and (iv) a weighted reference channel decrease metric. In some non-limiting aspects, the calculated MEP value may be passed through a filter such as, for example and without limitation, a Kalman Filter.

In some aspects, the smaller the MEP is, the worse the electronic performance of the sensor 100 is. In some non-limiting aspects, the MEP may always be between 0 and 1. In some non-limiting aspects, the weights for one or more of the spike metric, reference channel instability metric, diagnostic drift metric, and reference channel decrease metric may be specified as, for example and without limitation, 1, 1, 1, and 1, respectively. However, this is not required, and, in some alternative aspects, the transceiver 101 may use one or more different weights. In some aspects, these weights may be optimized for different sensor configurations. In some aspects, the smaller the weight for a parameter is, the more influence the parameter has on the sensor electronic performance.

In some non-limiting aspects, the transceiver 101 may calculate MEP and then pass the calculated value through a filter because the calculated MEP may contain noise (e.g., noise introduced by a large temperature swing). In some aspects, the filter may be a Kalman Filter. In some non-limiting aspects, the transceiver 101 may use a Kalman Filter similar to the one described at http://www.cs.unc.edu/~welch/kalman/kalmanIntro.html, except that the measurement noise R may be set equal to $R_0$. In some non-limiting aspects, $R_0$ may be equal to, for example and without limitation, 3. In some aspects, the rest parameter update may follow a standard Kalman Filter procedure. In some aspects, the Kalman-filtered MEP may be an initial value of 1 (i.e., the filtered MEP may always start with 1 at the very beginning of the sensor life).

In some aspects, the transceiver 101 may store MEP values (e.g., filtered MEP values) in an MEP buffer (e.g., in memory 922). In some non-limiting aspects, the transceiver 101 may convey the latest MEP to the analyte sensor 100 (e.g., for storage in a non-volatile memory of the sensor 100, such as an EEPROM). In some aspects, the transceiver 101 may convey the most recent MEP value to the sensor 100 periodically (e.g., every 12 or 24 hours) and in case of sensor electronic performance deficiency (see below). However, in some alternative aspects, the MEP values may be conveyed to the sensor 100 for storage in the sensor memory immediately regardless of the time. In some aspects, the transceiver 101 may obtain previous MEP values from the memory of the sensor 100 in the event MEP values in the transceiver 101 (e.g., in an MEP buffer in the memory 922) are deleted (e.g., during a transceiver reset).

In some aspects, after calculating MEP, the analyte monitoring system 50 may use the calculated MEP to determine whether the electronic performance of the analyte sensor 100 is unsuitable for continuous analyte monitoring. In some aspects, the transceiver 101 of the analyte monitoring system 50 may calculate MEP and determine whether the sensor electronic performance is unsuitable for continuous analyte monitoring. In some aspects, the transceiver 101 will determine that the electronic performance of the analyte sensor 100 is deficient if MEP is below an MEP deficiency threshold. In some non-limiting aspects, the MEP deficiency threshold may be, for example and without limitation, 0.35. In some non-limiting aspects, the MEP deficiency threshold may be within a range from 0.99 to zero, and this MEP range should be understood as describing and disclosing all MEP values (including all decimal or fractional MEP values) and sub-ranges within this range.

In some aspects, the transceiver 101 will determine that the analyte sensor 100 should be retired if MEP is below the MEP deficiency threshold for at least a period of time. In some non-limiting aspects, the period of time may be, for example and without limitation, 3600 seconds. In some non-limiting aspects, the period of time may be within a range from one second to 10 days, and this period of time range should be understood as describing and disclosing all periods of time (including all decimal or fractional seconds) and sub-ranges within this range. In some aspects, the transceiver 101 will only determine that the electronic performance of the analyte sensor 100 is deficient if (i) MEP is below the MEP deficiency threshold for at least the period of time and (ii) an initialization period (e.g., a period of, for example and without limitation, 1,728,000 seconds or 864,000 seconds, which may represent the maximum time the analyte sensor 100 would require for hydration after implantation) has passed since the analyte sensor 100 was implanted. In some non-limiting aspects, the transceiver 101 may approximate the sensor implant time as the time at which the transceiver 101 is paired with the analyte sensor 100, which typically occurs immediately after implant.

In some aspects, the MEP values for each of the sensors may start at 1. In some non-limiting aspects, the electronic performance of the sensors is determined to be deficient when the MEP goes below the MEP deficiency threshold, and, for each sensor, the corresponding transceiver stops conveying analyte level information (e.g., to a display device for display) when the transceiver determines the sensor electronic performance to be deficient.

In some aspects, if the transceiver 101 determines that the electronic performance of the analyte sensor 100 is deficient, the analyte monitoring system 50 may consider the sensor 100 to no longer be suitable for continuous analyte monitoring, and the transceiver 101 may trigger a sensor retirement alert, which the transceiver 101 may convey to the display device 105. In some aspects, if the sensor 100 is no longer be suitable for continuous analyte monitoring, the analyte monitoring system 50 may stop displaying calculated analyte levels.

Figure 4:
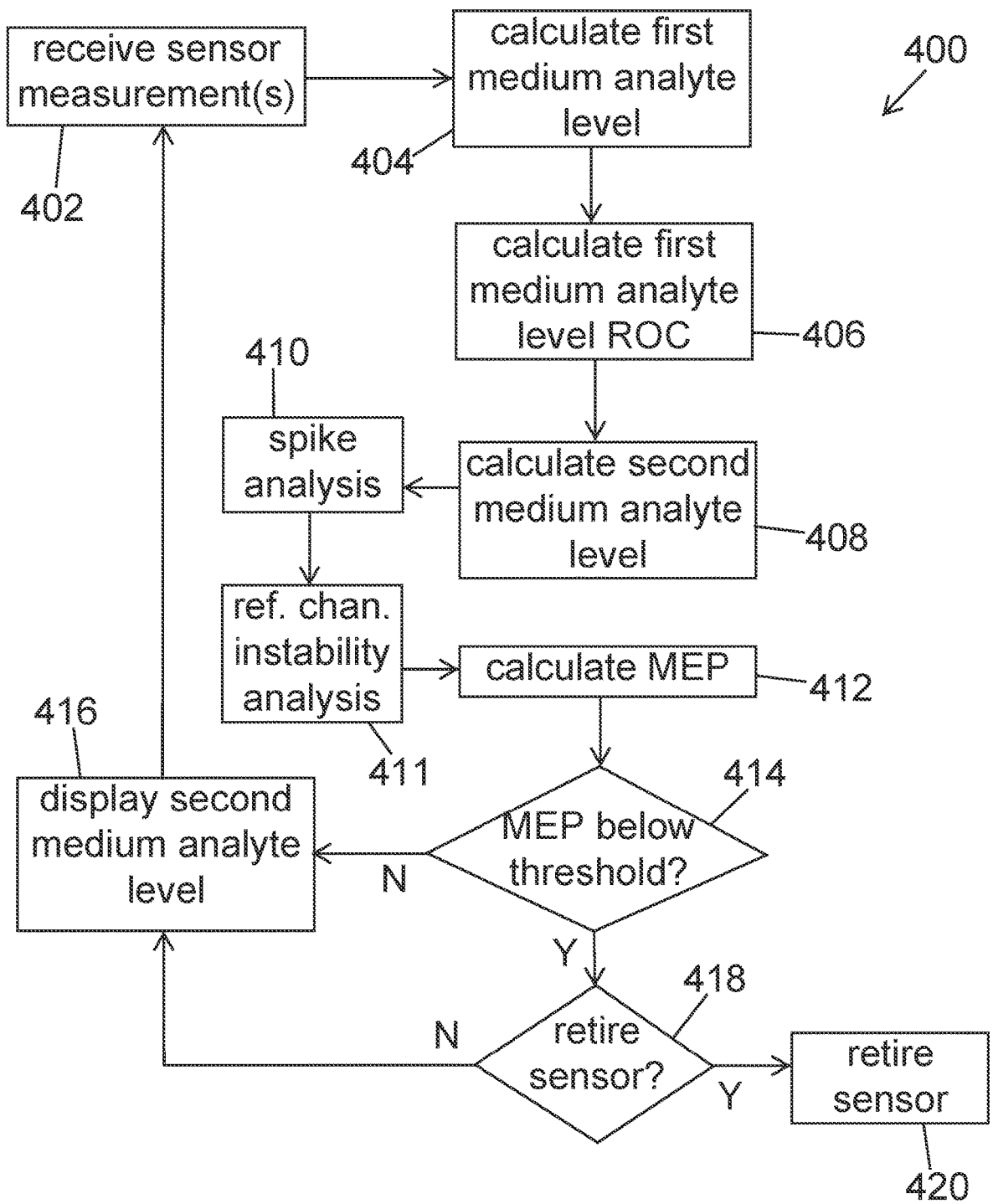
FIG. 4 is a flow chart illustrating an analyte monitoring process embodying aspects of the present invention.

FIG. 4 is a flow chart illustrating an analyte monitoring process 400 according to some non-limiting aspects. In some aspects, one or more steps of the process 400 may be performed by an analyte monitoring system, such as, for example, the analyte monitoring system 50. In some aspects, one or more steps of the process 400 may be performed by a transceiver, such as, for example, the transceiver 101. In some non-limiting aspects, one or more steps of the process 400 may be performed by a processor, such as, for example, the processor 920 of the transceiver 101.

In some aspects, the process 400 may include a step 402 in which the transceiver 101 receives one or more sensor measurements from the sensor 100. In some non-limiting aspects, the one or more sensor measurements may include, for example and without limitation, one or more light measurements and/or one or more temperature measurements. In some aspects, the transceiver 101 may receive the one or more sensor measurements after conveying a command (e.g., a measurement command or a read sensor data command) to the sensor 100. However, this is not required, and, in some alternative aspects, the sensor 100 may control when one or more sensor measurements are conveyed to the transceiver 101, or the sensor 100 may continuously convey sensor measurements to the transceiver 101. In some non-limiting aspects, the transceiver 101 may receive one or more sensor measurements periodically (e.g., every 1, 2, 5, 10, or 15 minutes).

In some aspects, the transceiver 101 may receive the one or more sensor measurements using the sensor interface of the transceiver 101. In some non-limiting aspects, the transceiver 101 may receive the one or more sensor measurements wirelessly. For example and without limitation, in some non-limiting aspects, the transceiver 101 may receive the one or more sensor measurements by detecting modulations in an electromagnetic wave generated by the sensor 100, e.g., by detecting modulations in the current flowing through the inductive element 103 of the transceiver 101. However, this is not required, and, in some alternative aspects, the transceiver 101 may receive the one or more sensor measurements via a wired connection to the sensor 100.

In some aspects, the one or more sensor measurements may be associated with a time stamp. In some non-limiting aspects, the transceiver 101 may receive the time stamp from the sensor 100. In some non-limiting aspects, the received one or more sensor measurements may include the time stamp. In some aspects, the time stamp may reflect the time at which the one or more sensor measurements were taken. However, it is not required that the transceiver 101 receive the time stamp from the sensor 100. For example, in some alternative aspects, the transceiver 101 may assign the time stamp to the one or more sensor measurements after receiving the one or more sensor measurements. In these aspects, the time stamp may reflect when the transceiver 101 received the one or more sensor measurements.

In some aspects, the process 400 may include a step 404 in which the transceiver 101 calculates a first medium analyte level (e.g., an ISF analyte level) using the one or more sensor measurements received from the sensor 100. In some aspects, the first medium analyte level may be a measurement of the amount or concentration of the analyte in the first medium (e.g., interstitial fluid) in proximity to the analyte sensor 100. In some non-limiting aspects, calculation of the first medium analyte level may include, for example and without limitation, some or all of the features described in U.S. application Ser. No. 13/937,871, filed on Jul. 9, 2013, now U.S. Pat. No. 9,414,775, which is incorporated by reference herein in its entirety.

In some aspects, the process 400 may include a step 406 in which the transceiver 101 calculates a first medium analyte level rate of change ("M1_ROC"). In some aspects, the transceiver 101 may calculate the M1_ROC using at least the first medium analyte level calculated in step 404 and one or more previously calculated first medium analyte levels (e.g., one or more first medium analyte levels calculated using previously received sensor measurements). In some non-limiting aspects, the transceiver 101 may calculate M1_ROC as the difference between the calculated first medium analyte level and the most recent previously calculated first medium analyte level divided by the time difference between a time stamp for the calculated first medium analyte level and a time stamp for the most recent previously calculated first medium analyte level. In other words, in some non-limiting aspects, M1_ROC may equal $(M1\_AL(n)-M1\_AL(n-1))/(T(n)-T(n-1))$, where M1_AL(n) is the calculated first medium analyte level, M1_AL(n-1) is the most recent previously calculated first medium analyte level, and T(n) and T(n-1) are the time stamps. However, this is not required, and, in some alternative aspects, the transceiver 101 may calculate M1_ROC using the calculated first medium analyte level and a plurality of the most recent previously calculated first medium analyte levels. In some non-limiting aspects, the plurality of the most recent previously calculated ISF analyte levels may be, for example and without limitation, the previous two calculated first medium analyte levels, the previous 20 calculated first medium analyte levels, or any number of previously calculated ISF analyte levels in between (e.g., the previous 5 calculated first medium analyte levels). In other alternative aspects, to calculate M1_ROC, the transceiver 101 may use the calculated first medium analyte level and the previously calculated first medium analyte levels that were calculated during a time period. In some non-limiting aspects, the time period may be, for example and without limitation, the last one minute, the last 60 minutes, or any amount of time in between (e.g., the last 25 minutes). In some aspects where the transceiver 101 uses the calculated first medium analyte level and more than one previously calculated first medium analyte levels to calculate M1_ROC, the transceiver 101 may use, for example, linear or non-linear regression to calculate M1_ROC.

In some aspects, the process 400 may include a step 408 in which the transceiver 101 calculates a second medium analyte level (e.g., a blood analyte level). In some aspects, the transceiver 101 may calculate the second medium analyte level by performing a lag compensation. In some aspects, the transceiver 101 may calculate the second medium analyte level using at least the first medium analyte level and the M1_ROC calculated in steps 404 and 406, respectively. In some aspects, the transceiver 101 may calculate the second medium analyte level using a conversion function. In some non-limiting aspects, the transceiver 101 may calculate the second medium analyte level as $M1\_ROC/p_2+(1+p_3/p_2)*M1$ analyte, where M1_ROC is the rate of change of the first medium analyte level, $p_2$ is analyte diffusion rate, $p_3$ is the analyte consumption rate, and M1 analyte is the calculated first medium analyte level.

In some aspects, the process 400 may include a step 410 in which the transceiver 101 performs a spike analysis to determine whether the second medium analyte level calculated in step 408 is a potentially erroneous spike. In some non-limiting aspects, the transceiver 101 may keep track of the number of calculated second medium analyte levels that have been determined to be potentially erroneous spikes. In some non-limiting aspects, if the transceiver 101 determines that the calculated second medium analyte level is a spike, the transceiver 101 may increment a count of the number of calculated second medium analyte levels that have been determined to be potentially erroneous spikes. In some non-limiting aspects, if the transceiver 101 determines that the calculated second medium analyte level is a spike, the transceiver 101 may calculate an alternative second medium analyte level. A non-limiting example of a spike analysis process that may be performed in step 410 is described below with reference to FIG. 5.

In some aspects, the process 400 may include a step 411 in which the transceiver 101 performs a reference channel instability analysis to detect the presence of reference channel instability. In some aspects, the reference channel instability analysis may include comparing a current temperature corrected reference light measurement with the previous temperature corrected reference light measurement nearest in time to the most-recent calibration point. In some non-limiting aspects, the temperature corrected reference light measurement for the reference channel instability analysis may be defined as equal to the reference light measurement* (1+max(0, TempCorrectionFactor*Ref_cz/

RefInstability_DefaultCz)*(temperature−37)). In some aspects, the reference light measurement may be a measurement of the amount of reflection light 333 received by the photodetector 226 and digitized by an analog to digital converter of the analyte sensor 100. In some aspects, the temperature measurement may be a measurement of the sensor temperature by the temperature sensor 670 of the analyte sensor 100. In some non-limiting aspects, the temperature measurement may have been digitized by an analog to digital converter of the analyte sensor 100. In some aspects, the reference light and temperature measurements may be part of the one or more sensor measurements received by the transceiver 101 in step 402. In some non-limiting aspects, the TempCorrectionFactor may be, for example and without limitation, 0.009. In some non-limiting aspects, the Ref_cz may be a temperature correction factor for the light source 108 of the reference channel of the sensor 100. The Ref_cz may vary from one sensor to another, may be estimated during a sensor quality control process after manufacturing of the sensor 100 and before implantation or insertion of the sensor 100, and may be, for example and without limitation, 0.0054122 or 0.0063641. In some non-limiting aspects, the RefInstability_DefaultCz may be a parameter having a value of, for example and without limitation, 0.0168.

In some non-limiting aspects, the transceiver 101 may determine that reference channel instability exists if (i) less than a threshold period of time (e.g., 1 day) has passed between the current sensor measurements and the most-recent calibration point and (ii) the absolute difference between the current temperature corrected RefOnOff_ADC with the temperature corrected RefOnOff_ADC nearest to the most-recent calibration point is less than or equal to an instability threshold (e.g., 0.05). In some non-limiting aspects, the transceiver 101 may only determine that reference channel instability exists if the conditions (i) and (ii) are met for a number (e.g., 3) of consecutive sensor measurements.

In some non-limiting aspects, in step 411, if reference channel instability is detected, the transceiver 101 may perform one or more of the following: (i) blind the analyte monitoring system 50 by not displaying any calculated analyte levels, which may be erroneous, (ii) convey a sensor check communication (e.g., a sensor check alert, alarm, or notification) to the display device 105 for display of the communication to a user, (iii) clear a calibration buffer of the transceiver 101 that stores one or more calibration points (e.g., one or more reference analyte measurements received from the display device 105), and (iv) have the analyte monitoring system 50 return to an initialization phase. In some aspects, in the initialization phase, the transceiver 101 may receive one or more sensors measurements (e.g., periodically such as, for example and without limitation, every 2, 5, or 10 minutes) and calculate second medium analyte levels, but the system 50 may not display the calculated second medium analyte levels (e.g., the transceiver 101 may not convey analyte levels to the display device 105). In some aspects, in the initialization phase, the transceiver 101 may receive references measurements more frequently than during a normal calibration phase (e.g., approximately every 2 hours as opposed to approximately every 12 hours). The transceiver 101 may use the reference measurements as calibration points for the calibration buffer. In some aspects, system 50 may stay in the initialization phase for a certain amount of time (e.g., 2 days) or until the transceiver 101 receives a certain number of reference measurements (e.g., 10 reference measurements). In some aspects, after the completion of the initialization phase, the system 50 may proceed to the normal calibration phase and display calculated analyte measurements.

In some aspects, the process 400 may include a step 412 in which the transceiver 101 calculates the metric for electronic performance (MEP). In some aspects, the transceiver 101 may store the calculated MEP value in an MEP buffer (e.g., in memory 922). In some aspects, calculating the MEP may take into account measures of one or more of spikes in the calculated analyte levels, reference channel instability, diagnostic drift, and reference channel decreases. A non-limiting example of a process that may be performed in step 412 to calculate the MEP is described below with reference to FIG. 6.

In some aspects, the process 400 may include a step 414 in which the transceiver 101 compares the calculated MEP to the MEP deficiency threshold (e.g., 0.35). If the comparison of the calculated MEP to the MEP deficiency threshold indicates that the sensor performance is deficient (e.g., if the assessment of sensor performance is less than the deficiency threshold), the process 400 may proceed to a step 418 in which the transceiver 101 determines whether the sensor 100 should be retired (e.g., whether the sensor 100 has reached the end of its functional life). However, if the comparison in step 414 does not indicate that the sensor performance is deficient, the process 400 may proceed to a display step 416.

In some aspects, the process 400 may include the step 416 in which the transceiver 101 displays a calculated second medium analyte level. In some aspects, the second medium analyte level displayed in step 416 may be the second medium analyte level calculated in step 408. However, in aspects in which the spike analysis step 410 calculates an alternative second medium level if a spike is detected, the second medium analyte level displayed in step 416 may be (a) the second medium analyte level calculated in step 408 if no spike is detected in step 410 or (b) the alternative second medium analyte level calculated in step 410 if a spike is detected in step 410. In some aspects, in step 416, the transceiver 101 may display the analyte level on the display 924. In some aspects, in step 416, the transceiver 101 may additionally or alternatively display the second medium analyte level by conveying it to the display device 105, and the display device 105 may additionally or alternatively display the calculated second medium analyte level.

In some aspects, the process 400 may include the step 418 in which the transceiver 101 determines whether the sensor 100 should be retired (e.g., whether the sensor 100 has reached the end of its functional life). In some aspects, the transceiver 101 will determine that the analyte sensor 100 should be retired if MEP is below the MEP deficiency threshold for at least a period of time (e.g., 3600 seconds). In some aspects, the transceiver 101 will only determine that the electronic performance of the analyte sensor 100 is deficient if (i) MEP is below the MEP deficiency threshold for at least the period of time and (ii) an initialization period (e.g., 1,728,000 seconds or 864,000 seconds) has passed since the analyte sensor 100 was implanted. In some aspects, if the transceiver 101 determines that the sensor 100 need not be retired, the process 400 may proceed from the step 418 to the display step 416. In some aspects, if the transceiver 101 determines that the sensor 100 should be retired, the process 400 may proceed from the step 418 to a sensor retirement step 420.

In some aspects, in the sensor retirement step 420, the transceiver 101 may display a sensor retirement indication. In some aspects, the transceiver 101 may display the sensor retirement indication by conveying a sensor retirement communication (e.g., a sensor retirement alarm, alert, or notification) to the display device 105. In some non-limiting aspects, the transceiver 101 may additionally or alternatively blind the sensor output (e.g., stop conveying calculated second medium analyte levels to the display device 105 for display). In some aspects, in response to receiving the sensor retirement communication, the display device 105 may display an indication that the sensor needs to be replaced and/or that analyte levels will not be displayed until after the sensor 100 is replaced.

Figure 5:
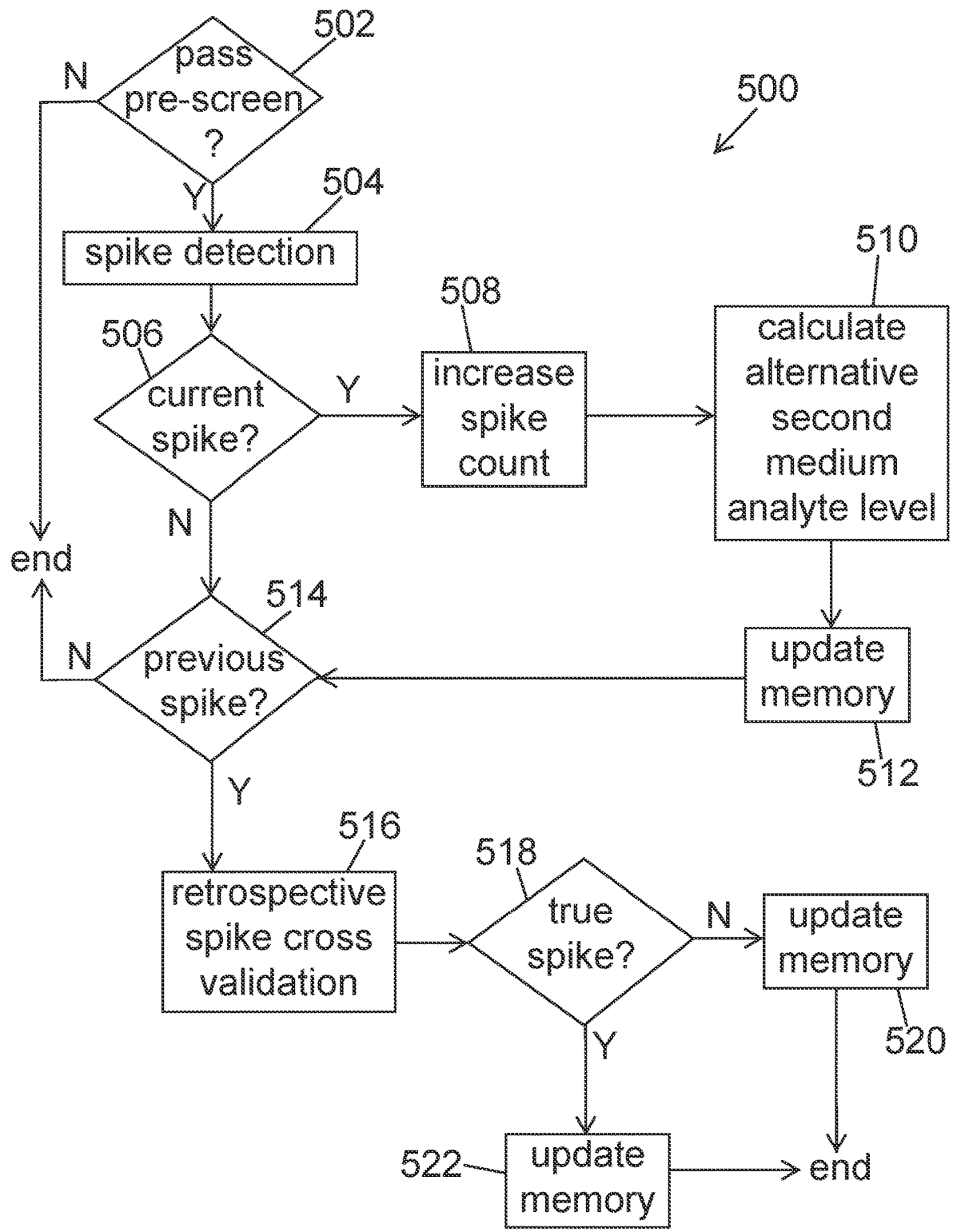
FIG. 5 is a flow chart illustrating a spike analysis process embodying aspects of the present invention.

FIG. 5 is a flow chart illustrating a spike analysis process 500, which may be performed during the spike analysis step 410 of the analyte monitoring process 400 illustrated in FIG. 4. In some aspects, the transceiver 101 may perform one or more steps of the spike analysis process 500. In some non-limiting aspects, the processor 920 of the transceiver 101 may perform one or more steps of the spike analysis process 500.

In some aspects, the spike analysis process 500 may include a step 502 in which the transceiver 101 determines whether one or more prescreening criteria are met. In some non-limiting aspects, the prescreening criteria may include one or more of: (i) that at least three calculated second medium analyte levels are stored in the transceiver 101 (e.g., in an analyte level buffer of memory 922), (ii) that one or more calculated analyte levels (e.g., the calculated first medium analyte level and the calculated second medium analyte level) are valid, and (iii) that the calculated that the transceiver 101 has not performed a calibration recently (e.g., since the calculating the previous second medium analyte level). In some non-limiting aspects, one or more calculated analyte levels may be determined to be valid if the calculated analyte levels are between 40 and 400 mg/dL. In some aspects, if the prescreening criteria are met, the spike analysis process 500 may proceed to a spike detection step 504.

In some aspects, in the spike detection step 504, the transceiver 101 may determine whether the calculated second medium analyte level (e.g., the second medium analyte level calculated in step 408 of the process 400 illustrated in FIG. 4) is a spike. In some aspects, determining whether a calculated second medium analyte level is a spike may include one or more of (i) determining whether the first medium analyte level is changing faster than a first medium analyte level rate of change threshold ("M1_ROC threshold"), (ii) determining whether the second medium analyte level is changing faster than a second medium analyte level rate of change threshold ("M2_ROC threshold"), (iii) determining whether a difference between the first medium analyte level rate of change and the previous first medium analyte level rate of change is greater than a first medium analyte level rate of change difference threshold ("M1_ROC difference threshold"), and (iv) determining whether a difference between the second medium analyte level rate of change and the previous second medium analyte level rate of change is greater than a second medium analyte level rate of change difference threshold ("M2_ROC difference threshold"). In some non-limiting aspects, the transceiver 101 may determine that the second medium analyte level is a spike only if all four of the thresholds are exceeded. However, this is not required, and, in some alternative aspects, the transceiver 101 may determine that the second medium analyte level is a spike if fewer than all of the thresholds are exceeded (e.g., only if three or more thresholds are exceeded, only if two more thresholds are exceeded, or if any threshold is exceeded).

In some aspects, determining whether the first medium analyte level is changing faster than a first medium analyte level rate of change threshold in step 504 may include comparing the M1_ROC (e.g., the M1_ROC calculated in step 406 and used to calculate the second medium analyte level in step 408 of the process 400 illustrated in FIG. 4) to the M1_ROC threshold. In some aspects, determining whether the first medium analyte level is changing faster than the M1_ROC threshold may include comparing the absolute value of M1_ROC to the M1_ROC threshold. In some non-limiting aspects, the M1_ROC threshold may be, for example and without limitation, 1.5 mg/dL/min.

In some aspects, determining whether the second medium analyte level is changing faster than the M2_ROC threshold in step 504 may include calculating the rate of change of the second medium analyte level ("M2_ROC"). In some non-limiting aspects, the transceiver 101 may calculate M2_ROC as the difference between the calculated second medium analyte level and most recent previously calculated second medium analyte level divided by the time difference between a time stamp for the calculated second medium analyte level and a time stamp for the most recent previously calculated second medium analyte level. In other words, in some non-limiting aspects, M2_ROC may equal (M2_AL(n)−M2_AL(n−1))/(T(n)−T(n−1)), where M2_AL(n) is the calculated second medium analyte level, M2_AL(n−1) is the most recent previously calculated second medium analyte level, and T(n) and T(n−1) are the time stamps. However, this is not required, and, in some alternative aspects, the transceiver 101 may calculate M2_ROC using the calculated second medium analyte level and a plurality of the most recent previously calculated second medium analyte levels.

In some aspects, determining whether the second medium analyte level is changing faster than the M2_ROC threshold in step 504 may include comparing M2_ROC to the M2_ROC threshold. In some aspects, determining whether the second medium analyte level is changing faster than the M2_ROC threshold in step 504 may include comparing the absolute value of M2_ROC to the M2_ROC threshold. In some non-limiting aspects, the M2_ROC threshold may be, for example and without limitation, 4 mg/dL/min.

In some aspects, determining whether a difference between the current M1_ROC and the previous M1_ROC is greater than the M1_ROC difference threshold in step 504 may include calculating the difference between the current M1_ROC (i.e., M1_ROC(n)) and the previous M1_ROC (i.e., M1_ROC(n−1)). In some aspects, determining whether a difference between the current M1_ROC and the previous M1_ROC is greater than the M1_ROC difference threshold in step 504 may include comparing the difference between the current M1_ROC and the previous M1_ROC to the M1_ROC difference threshold. In some aspects, determining whether a difference between the first medium analyte level rate of change and the previous first medium analyte level rate of change is greater than the M1_ROC difference threshold may include comparing the absolute value of the difference between the current M1_ROC and the previous M1_ROC to the M1_ROC difference threshold. In some non-limiting aspects, the M1_ROC difference threshold may be, for example and without limitation, 2 mg/dL/min.

In some aspects, determining whether a difference between the current M2_ROC and the previous M2_ROC is greater than the M2_ROC difference threshold in step 504 may include calculating the difference between the current M2_ROC (i.e., M2_ROC(n)) and the previous M2_ROC (i.e., M2_ROC(n−1)). In some aspects, determining whether a difference between the current M2_ROC and the previous M2_ROC is greater than the M2_ROC difference threshold in step 504 may include comparing the difference between the current M2_ROC and the previous M2_ROC to the M2_ROC difference threshold. In some aspects, determining whether a difference between the current M2_ROC and the previous M2_ROC is greater than the M2_ROC difference threshold may include comparing the absolute value of the difference between the current M2_ROC and the previous M2_ROC to the M2_ROC difference threshold. In some non-limiting aspects, the M2_ROC difference threshold may be, for example and without limitation, 4 mg/dL/min.

In some aspects, the spike analysis process 500 may include a step 506 in which the transceiver 101 determines whether the current calculated second medium analyte level (i.e., M2_AL(n)) was determined to be spike in step 504. In some aspects, if the current calculated second medium analyte level was determined to be a spike, the process 500 may proceed from step 506 to one or more of steps 508, 510, and 512. In some aspects, if the current calculated second medium analyte level was not determined to be a spike, the process 500 may proceed from the step 506 to a step 514.

In some aspects, the spike analysis process 500 may include a step 508 in which the transceiver 101 increments a count of the number of calculated second medium analyte levels that have been determined to be spikes. In some aspects, the spike count may be stored in a memory (e.g., memory 922) of the transceiver 101.

In some aspects, the spike analysis process 500 may include a step 510 in which the transceiver 101 calculates an alternative second medium analyte level. In some aspects, the transceiver 101 may display the alternative second medium analyte level (e.g., convey the alternative second medium analyte level to the display device 105) instead of the second medium analyte level calculated in step 408 and determined to be a spike in step 504. In some aspects, calculating the alternative second medium analyte level may include calculating one or more of (i) a predicted second medium analyte level, (ii) an M2_ROC threshold-limited second medium analyte level, and (iii) a dynamic Kalman filtered second medium analyte value per noise variance. In some non-limiting aspects, the predicted second medium analyte level may be calculated using at least the previous calculated second medium analyte level and the previous M2_ROC. For example and without limitation, in one non-limiting embodiment, predicted M2_AL(n)=M2_AL(n−1)+(M2_ROC(n−1)*(T(n)−T(n−1))), where predicted M2_AL(n) is the predicted second medium analyte level, M2_AL(n−1) is the previous calculated second medium analyte level, M2_ROC(n−1) is the previous second medium analyte level rate of change, and T(n) and T(n−1) are the time stamps for the current and previous second medium analyte levels, respectively. In some non-limiting aspects, the M2_ROC threshold-limited second medium analyte level may be calculated using at least the previous calculated second medium analyte level and the M2_ROC threshold. For example and without limitation, in one non-limiting embodiment, threshold-limited M2_AL(n)= M2_AL(n−1)+(M2_ROC threshold*(T(n)−T(n−1))) if M2_ROC(n) is positive, and threshold-limited M2_AL(n)= M2_AL(n−1)−(M2_ROC threshold*(T(n)−T(n−1))) if M2_ROC(n) is negative, where threshold-limited M2_AL(n) is the M2_ROC threshold-limited second medium analyte level, M2_AL(n−1) is the previous calculated second medium analyte level, M2_ROC threshold is the second medium analyte level rate of change threshold, T(n) and T(n−1) are the time stamps for the current and previous second medium analyte levels, respectively, and M2_ROC(n) is the current second medium analyte level rate of change. In some non-limiting aspects, the alternative second medium analyte level may be the average of two or more of (i) the predicted second medium analyte level, (ii) the M2_ROC threshold-limited second medium analyte level, and (iii) the dynamic Kalman filtered second medium analyte value per noise variance.

In some aspects, the spike analysis process 500 may include a step 512 in which the transceiver 101 stores the alternative second medium analyte level in the transceiver 101 (e.g., in the analyte level buffer of memory 922). In some non-limiting aspects, the transceiver 101 may additionally store an indication that stored value is an alternative value. In some aspects, the transceiver 101 may store both the second medium analyte level calculated in step 408 of process 400 and the alternative second medium analyte level calculated in step 510. In some alternative aspects, the transceiver 101 may store the alternative second medium analyte level in place of the second medium analyte level, which was determined to be a spike in step 504. In some aspects, the process 500 may proceed from steps 508, 510, and 512 to the step 514.

In some aspects, in step 514, the transceiver 101 may check whether the previous calculated second medium analyte level (i.e., M2_AL(n)) was determined to be spike (e.g., in the previous iteration of step 504). In some aspects, if the previous calculated second medium analyte level was determined to be a spike, the process 500 may proceed from step 514 to one or more of steps 516, 518, 520, and 522.

In some aspects, the spike analysis process 500 may include a step 516 in which the transceiver 101 performs a retrospective spike cross validation that uses at least the current second medium analyte level to determine whether a previous second medium analyte level that was determined to be a spike truly was a spike. In some aspects, in step 516, the transceiver 101 may check whether the absolute difference between (a) the average of the current second medium analyte level and the second medium analyte level before the previous second medium analyte level and (b) the previous second medium analyte level ("the first absolute difference") is greater than or equal to a first threshold. In some aspects, the transceiver 101 may additionally or alternatively check whether the absolute difference between (a) the average of the current first medium analyte level and the first medium analyte level before the previous first medium analyte level and (b) the previous first medium analyte level ("the second absolute difference") is greater than or equal to a second threshold. In some non-limiting aspects, the first and second thresholds may be, for example and without limitation, 10 mg/dL and 8.5 mg/dL, respectively. In some aspects, the transceiver 101 may determine that the previous second medium analyte level was truly a spike if any of the first absolute difference is greater than or equal to the first threshold, the second absolute difference is greater than or equal to the second threshold, or both. In some non-limiting aspects, the transceiver 101 may determine that the previous second medium analyte level was not truly a spike if the first absolute difference is less than the first threshold and the second absolute difference is less than the second threshold.

In some aspects, the spike analysis process 500 may include a step 518 in which the transceiver 101 determines whether the previous second medium analyte level (i.e., M2_AL(n−1)) was determined to be a true spike in step 516. In some aspects, if the previous second medium analyte level was determined to not be a true spike, the process 500 may proceed from step 518 to a step 520 in which the transceiver 101 may update the analyte level buffer (e.g., in the of memory 922) by deleting the previous alternative second medium analyte level (e.g., the alternative M2_AL(n−1) previously calculated in step 510) and leaving the previous second medium analyte level (e.g., the M2_AL(n−1) previously calculated in step 408). In some alternative aspects, the process 500 may not include the step 520, and, if the previous second medium analyte level was determined to not be a true spike, the process 500 may do nothing (i.e., proceed directly from step 518 to "end" in FIG. 5). In some aspects, if the previous second medium analyte level was determined to be a true spike, the process 500 may proceed from step 518 to a step 522 in which the transceiver 101 may update the analyte level buffer (e.g., in the of memory 922) by deleting the previous second medium analyte level (e.g., the M2_AL(n−1) previously calculated in step 408) and leaving the previous alternative second medium analyte level (e.g., the alternative M2_AL(n−1) previously calculated in step 510).

Figure 6:
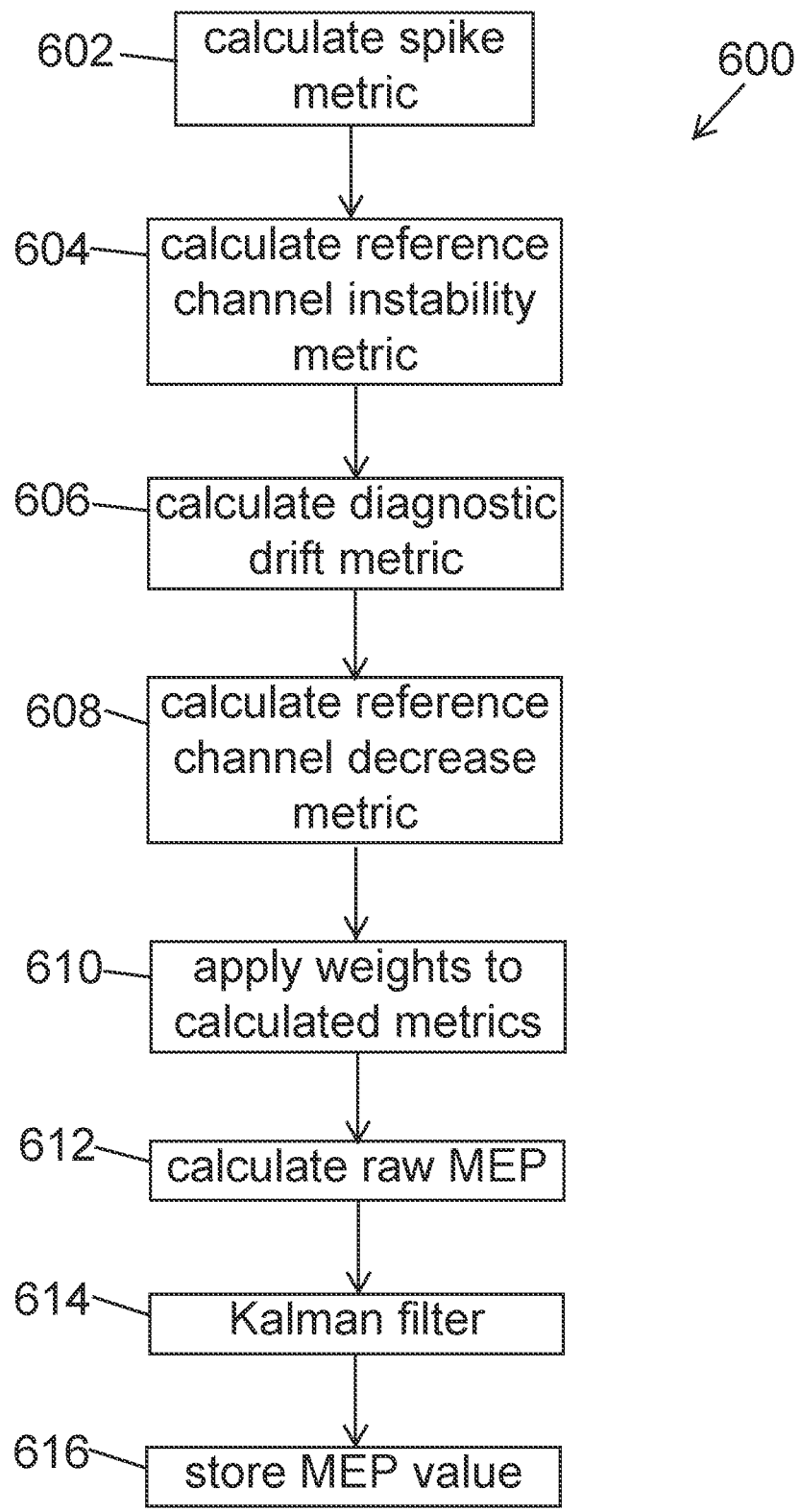
FIG. 6 is a flow chart illustrating a process for calculating a metric for electronic performance embodying aspects of the present invention.

FIG. 6 is a flow chart illustrating an MEP calculation process 600, which may be performed during the MEP calculation step 412 of the analyte monitoring process 400 illustrated in FIG. 4. In some aspects, the transceiver 101 may perform one or more steps of the MEP calculation process 600. In some non-limiting aspects, the processor 920 of the transceiver 101 may perform one or more steps of the MEP calculation process 600.

In some aspects, the MEP calculation process 600 may include a step 602 in which the transceiver 101 calculates a spike metric. In some aspects, the spike metric may quantify the noise level in the calculated analyte calculations, which may be displayed by the display device 105. In some non-limiting aspects, the spike metric may range, for example and without limitation, from 0 to 1 with 1 being its default value and representing no noise.

In some aspects, the transceiver 101 may calculate the spike metric based on the number of detected spikes in the calculated analyte levels. In some aspects, the spikes may be detected in the spike analysis step 410 of the process 400 illustrated in FIG. 4. In some non-limiting aspects, the spikes may be detected in the spike detection step 504 of the spike analysis process 500 illustrated in FIG. 5, which may be performed during the spike analysis step 410 of the process 400 illustrated in FIG. 4. In some aspects, the number of detected spikes may be tracked using the spike count incremented in step 508 each time a spike is detected.

In some non-limiting aspects, the transceiver 101 may calculate the spike metric as the maximum value of (a) zero and (b) the number of calculated second medium analyte levels minus the spike metric weight multiplied by the number of detected spikes in the calculated second medium analyte levels divided by the number of calculated second medium analyte levels. In some non-limiting aspects, the transceiver 101 may use the number of MEP values that the transceiver 101 has calculated (e.g., in step 412) and stored in a memory of the transceiver 101 (i.e., the MEP buffer size) as indicative of the number of calculated second medium analyte levels. However, this is not required, and, in some alternative aspects, the transceiver 101 may use a different value (e.g., the number of calculated second medium analyte levels stored in an analyte level buffer of the transceiver 101 ("analyte level buffer size")) as indicative of the number of calculated second medium analyte levels. In some aspects, the spike metric may be calculated as max(0, (MEP buffer size−spike_metric_weight*number of detected spikes)/MEP buffer size). In some alternative aspects, the spike metric may be calculated as max(0, (analyte level buffer size−spike_metric_weight*number of detected spikes)/analyte level buffer size). In some non-limiting aspects, the spike_metric_weight may be, for example and without limitation, 2.25.

In some aspects, the MEP calculation process 600 may include a step 604 in which the transceiver 101 calculates a reference channel instability metric. In some aspects, the reference channel instability metric may quantify the stability of the reference channel. In some non-limiting aspects, the reference channel instability metric may range, for example and without limitation, from 0 to 1 with 1 being its default value and representing perfect reference channel stability.

In some non-limiting aspects, in step 604, if the transceiver 101 does not determine that reference channel instability exists in step 411 of the process 400, the transceiver 101 may calculate the current reference channel instability metric as equal to the previous reference channel instability metric. In other words, in some aspects, if the transceiver 101 has not determined that reference channel instability exists, the reference channel instability metric may not change. In some non-limiting aspects, in step 604, if the transceiver 101 determines that reference channel instability exists in step 411, the transceiver 101 may calculate the current reference channel instability metric as equal to min(1, max(0, previous reference channel instability metric−(1/instability scaler))). In some non-limiting aspects, the instability scaler may be, for example and without limitation, 76.

In some aspects, the MEP calculation process 600 may include a step 606 in which the transceiver 101 calculates a diagnostic drift metric. In some aspects, the diagnostic drift metric may quantify the extent to which a diagnostic measurement has drifted from its factory value (i.e., the diagnostic measurement value during a sensor quality control process after manufacturing of the sensor 100 and before implantation or insertion of the sensor 100). In some non-limiting aspects, the diagnostic measurement may be, for example and without limitation, the electronic offset of the measurement system (e.g., a measurement of the output of a transimpedance amplifier of the sensor 100 with no photodetector connected to the transimpedance amplifier). In some non-limiting aspects, the diagnostic drift metric may range from 0 to 1 with 1 being its default value and representing that no diagnostic drift has occurred. In some non-limiting aspects, the transceiver 101 may calculate the diagnostic drift metric as equal to min(1, max(0, (maximumDriftThreshold−drift value)/(maximumDriftThreshold−driftThreshold))), where the drift value is equal to the absolute value of (diagnostic measurement−factoryDiagnostic), and the factoryDiagnostic value is factory value of the diagnostic measurement. In some non-limiting aspects, the maximumDriftThreshold may be, for example and without limitation, 10. In some non-limiting aspects, the driftThreshold may be, for example and without limitation, 4.

In some aspects, the MEP calculation process 600 may include a step 608 in which the transceiver 101 calculates a reference channel decrease metric. In some aspects, the reference channel decrease metric may quantify the extent to which the signal in the reference channel of the sensor 100 has decreased. In some non-limiting aspects, a decrease in the signal in the reference channel may reflect a dimming of the excitation light 329 emitted by light source 108. In some non-limiting aspects, the reference channel decrease metric may ranges from 0 to 1 with 1 being its default value and representing excitation light 329 at its normal state. In some non-limiting aspects, the transceiver 101 may calculate the reference channel decrease metric as equal to min(1, max(0, (mean temperature corrected reference light measurement/ POSTGRAFT_REF_s0_37−FILT_lowRefZeroValue)/ (FILT_lowRefOneValue−FILT_lowRefZeroValue))). In some non-limiting aspects, the POSTGRAFT_REF_s0_37 may be a reference value in nanoamps for the unbound glucose indicator at 37°. The POSTGRAFT_REF_s0_37 may vary from one sensor to another. The POSTGRAFT_REF_s0_37 may be, for example and without limitation, 36.2422 nA. In some non-limiting aspects, the FILT_lowRefZeroValue may be a reference value in nanoamps at which the reference channel decrease metric goes to zero. The FILT_lowRefZeroValue may be, for example and without limitation, 0.25. In some non-limiting aspects, the FILT_lowRefOneValue may be a reference value in nanoamps at which the reference channel decrease metric drops below 1. The FILT_lowRefOneValue may be, for example and without limitation, 0.7. In some aspects, the mean temperature corrected reference light measurement may be the average value of the temperature corrected reference light measurements stored in the transceiver 101 (e.g., in a physical value circular buffer of the memory 922). In some aspects, the temperature corrected reference light measurements may be equal to (1+Ref_cz*(temperature−37))*reference light measurement. In some non-limiting aspects, the Ref_cz may be a temperature correction factor for the light source 108 of the reference channel of the sensor 100. The Ref_cz may vary from one sensor to another, may be estimated during a sensor quality control process after manufacturing of the sensor 100 and before implantation or insertion of the sensor 100, and may be, for example and without limitation, 0.0054122 or 0.0063641. In some aspects, the reference light measurement may be a measurement of the amount of reflection light 333 received by the photodetector 226 and digitized by an analog to digital converter of the analyte sensor 100. In some aspects, the temperature measurement may be a measurement of the sensor temperature by the temperature sensor 670 of the analyte sensor 100. In some non-limiting aspects, the temperature measurement may have been digitized by an analog to digital converter of the analyte sensor 100. In some aspects, the reference light and temperature measurements may be part of the one or more sensor measurements received by the transceiver 101 in step 402.

In some aspects, the MEP calculation process 600 may include a step 610 in which the transceiver 101 applies weights to one or more of the spike metric, reference channel instability metric, diagnostic drift metric, and reference channel decrease metric calculated in steps 602, 604, 606, and 608, respectively. In some non-limiting aspects, the weights for one or more of the spike metric, reference channel instability metric, diagnostic drift metric, and reference channel decrease metric may be specified as, for example and without limitation, 1, 1, 1, and 1, respectively. However, this is not required, and, in some alternative aspects, the transceiver 101 may use one or more different weights. In some aspects, these weights may be optimized for different sensor configurations. In some aspects, the smaller the weight for a parameter is, the more influence the parameter has on the sensor electronic performance.

In some aspects, the MEP calculation process 600 may include a step 612 in which the transceiver 101 calculates a raw MEP value using one or more of the spike metric, reference channel instability metric, diagnostic drift metric, and reference channel decrease metric. In some non-limiting aspects, the raw MEP value may be the minimum value of two or more of the calculated metrics. In some non-limiting aspects, the raw MEP value may be the minimum value of three or more of the calculated metrics. In some non-limiting aspects, the raw MEP value may be the minimum value of the spike metric, reference channel instability metric, diagnostic drift metric, and reference channel decrease metric.

In some aspects, the MEP calculation process 600 may include a step 614 in which the transceiver 101 passes the calculated MEP value through a filter because the calculated MEP value may contain noise (e.g., noise introduced by errors in calibration points). In some aspects, the filter may be a Kalman Filter. In some non-limiting aspects, the transceiver 101 may use a Kalman Filter similar to the one described at http://www.cs.unc.edu/~welch/kalman/kalman-Intro.html, except that the measurement noise R may be set equal to $R_0$. In some non-limiting aspects, $R_0$ may be equal to, for example and without limitation, 3. In some aspects, the rest parameter update may follow a standard Kalman Filter procedure. In some aspects, the Kalman-filtered MEP may be an initial value of 1 (i.e., the filtered MEP may always start with 1 at the very beginning of the sensor life).

In some aspects, the MEP calculation process 600 may include a step 616 in which the transceiver 101 stores the MEP value (e.g., the filtered MEP value) in an MEP buffer of the transceiver 101 (e.g., in memory 922).

In some aspects, the analyte monitoring system 50 may predict the end of the functional life of an implanted analyte sensor 100. The manner in which an analyte sensor 100 implanted (fully or partially) in the body performs electronically may vary widely from sensor to sensor (and/or body to body). That is, a sensor's electronic performance over time may vary on a sensor by sensor basis (and/or on a patient by patient basis). Accordingly, in some aspects, the analyte monitoring system 50 may utilize information on the electronic performance of the analyte sensor 100 in order to predict the end of the functional life of analyte sensor 100.

In some aspects, the transceiver 101 of the analyte monitoring system 50 may predict the end of the functional life of the implanted analyte sensor 100. In other words, in some aspects, the transceiver 101 may predict the number the number of days remaining before the sensor performance is determined to be deficient for use in continuous analyte monitoring. In some aspects, the transceiver 101 may use the assessment of sensor electronic performance, which may be based on the metric for real time assessment of sensor electronic performance (MEP), to predict the sensor end of life (EOL). In some aspects, the transceiver 101 may use time since the sensor 100 was implanted (in addition to or as an alternative to the assessment of sensor electronic performance) to predict the sensor EOL.

In some aspects, the transceiver 101 may associate one or more sensor electronic performance assessment thresholds and/or one or more time since implant thresholds with one or more predictions of time remaining before sensor EOL. In some aspects, if the transceiver 101 calculates an MEP value less than a sensor electronic performance assessment threshold or if the time since implant exceeds a time since implant threshold, the transceiver 101 may predict the associated amount of time remaining before sensor EOL. In some aspects, the transceiver 101 may convey the predicted amount of time remaining before sensor EOL to the display device 105 (e.g., as a notification, alert, or alarm), and the display device 105 may display an appropriate indication of the predicted amount of time remaining before sensor EOL. See, e.g., FIGS. 7A-21 and the description thereof in U.S. patent application Ser. No. 15/786,954, filed on Oct. 18, 2017, which is incorporated by reference in its entirety.

In some aspects, the transceiver 101 may use one or more previous MEP values to train an autoregressive (AR) model.

In some non-limiting aspects, the transceiver 101 may begin using MEP values to train the AR model after a period of time (e.g., 20 days) has passed since sensor implant. As noted above, in some non-limiting aspects, the transceiver 101 may approximate the sensor implant time as the time at which the transceiver 101 is paired with the analyte sensor 100, which typically occurs immediately after implant. In some aspects, the transceiver 101 may use the AR model to predict one or more future MEP values. If, within a prediction time period (e.g., one, two, three, or four weeks), the predicted MEP values cross an MEP deficiency threshold (e.g., 0.35) at which sensor electronic performance is determined to be deficient (e.g., unsuitable for the continuous analyte monitoring), the transceiver 101 may use the time (e.g., day or hour) at which the predicted MEP crosses the MEP deficiency threshold as the predicted time of sensor EOL. See, e.g., FIGS. 22-23 and the description thereof in U.S. patent application Ser. No. 15/786,954, filed on Oct. 18, 2017, which is incorporated by reference in its entirety.

In some aspects, the transceiver 101 may begin predicting the sensor EOL after a particular time has passed since the sensor 100 was implanted (e.g., 60 days since implant). In some aspects, the transceiver 101 may predict sensor EOL periodically (e.g., after each calibration, daily, or every other day). In some aspects, the frequency at which sensor EOL is predicted may vary over time (e.g., the transceiver 101 may predict sensor EOL more frequently the closer the sensor gets to EOL). In some aspects, each time the transceiver 101 predicts sensor EOL (or each time the predicted time of sensor EOL is different than the previous predicted time of sensor EOL), the transceiver 101 may convey the predicted time of sensor EOL to the display device 105 (e.g., as a notification, alert, or alarm), and the display device 105 may display an appropriate indication of the predicted time of sensor EOL.

Aspects of the present invention have been fully described above with reference to the drawing figures. Although the invention has been described based upon these preferred aspects, it would be apparent to those of skill in the art that certain modifications, variations, and alternative constructions could be made to the described aspects within the spirit and scope of the invention. For instance, although aspects of the invention have been described above with respect to assessing sensor performance in an analyte monitoring system, in some alternative aspects, the assessing sensor performance of the present invention may be applied to different devices (e.g., temperature sensors, insulin pumps, or pacemakers) in different systems (e.g., temperature monitoring systems, insulin delivery systems, or cardiac contraction control systems). Also, although examples of particular parameters, thresholds, and time periods used in the sensor performance assessment have been described above, the parameters, thresholds, and time periods may vary from one embodiment to the next, and different parameters, thresholds, and time periods may be used for different sensors and/or system configurations.

In addition, although in some aspects the transceiver 101 of the analyte monitoring system 50 performs the sensor performance assessment, this is not required. In some alternative aspects, portions of or all of the sensor performance assessment may be performed by one or more of the analyte sensor 100 and display device 105.

Moreover, although some aspects have been described as using an AR model, this is not required. Some alternative aspects may use a different model, such as, for example and without limitation, linear regression, multivariate adaptive regression splines (MARS), exponential decay model, AR model with regularization, a fitted linear model, a non-linear (polynomial) model, or other predictive model defined by statically or analytically derived expressions.

What is claimed is:

1. An analyte monitoring system comprising:
an analyte sensor including an indicator having one or more detectable properties indicative of an amount or concentration of an analyte in a first medium in proximity to the indicator; and
a transceiver configured to:
receive one or more sensor measurements from the analyte sensor, wherein the one or more sensor measurements comprise at least a reference measurement and a signal measurement;
calculate an analyte level using at least the signal measurement;
detect whether reference channel instability is present using at least the reference measurement;
if reference channel instability is not detected, display the calculated analyte level;
if reference channel instability is detected, blind the analyte monitoring system by not displaying the calculated analyte level;
if reference channel instability is detected, transition the analyte monitoring system from a normal calibration phase to an initialization phase;
in the initialization phase, store calibration points more frequently than during the normal calibration phase; and
in the initialization phase, calculate but not display analyte levels.

2. The analyte monitoring system of claim 1, wherein:
the indicator comprises indicator molecules;
the analyte sensor further comprises (i) a light source configured to emit excitation light that interacts with the indicator molecules, (ii) one or more photodetectors sensitive to emission light emitted by the indicator molecules, and (iii) one or more photodetectors sensitive to excitation light reflected from the indicator as reflection light;
the signal measurement is indicative of a level of the emission light; and
the reference measurement is indicative of a level of the reflection light.

3. The analyte monitoring system of claim 1, wherein the transceiver, in detecting whether reference channel instability is present, is configured to compare a difference between the reference measurement and a previous reference measurement to an instability threshold.

4. The analyte monitoring system of claim 3, wherein the one or more sensor measurements further comprise a temperature measurement, and the transceiver is further configured to temperature correct the reference measurement using at least the temperature measurement.

5. The analyte monitoring system of claim 4, wherein the transceiver, in detecting whether reference channel instability is present, is configured to compare a difference between the temperature corrected reference measurement and a previous temperature corrected reference measurement to an instability threshold.

6. The analyte monitoring system of claim 5, wherein the transceiver, in detecting whether reference channel instability is present, is configured to compare a difference between a time of the temperature corrected reference measurement and a time of the previous temperature corrected reference measurement to a time threshold.

7. The analyte monitoring system of claim 1, further comprising a display device, wherein:
the transceiver is configured to display the calculated analyte level by conveying the calculated analyte level;
the display device is configured to receive and display the calculated analyte level; and
the transceiver, in blinding the analyte monitoring system, is configured to not convey the calculated analyte level to the display device.

8. The analyte monitoring system of claim 1, wherein the transceiver is further configured to, if reference channel instability is detected, convey a sensor check communication to the display device.

9. The analyte monitoring system of claim 1, wherein the transceiver comprises a calibration buffer that stores one or more calibration points, and the transceiver is further configured to, if reference channel instability is detected, clear the calibration buffer.

10. A method comprising:
receiving one or more sensor measurements from an analyte sensor of an analyte monitoring system, wherein the analyte sensor includes an indicator having one or more detectable properties indicative of an amount or concentration of an analyte in a medium in proximity to the indicator, and the one or more sensor measurements comprise at least a reference measurement and a signal measurement;
calculating an analyte level using at least the signal measurement;
detecting that reference channel instability is present using at least the reference measurement; and
if reference channel instability is detected, blinding the analyte monitoring system by not displaying the calculated analyte level;
if reference channel instability is detected, transitioning the analyte monitoring system from a normal calibration phase to an initialization phase, wherein:
in the initialization phase, the analyte monitoring system stores calibration points more frequently than during the normal calibration phase, and
in the initialization phase, the analyte monitoring system calculates but does not display analyte levels.

11. The method of claim 10, wherein:
the indicator comprises indicator molecules;
the analyte sensor further comprises (i) a light source configured to emit excitation light that interacts with the indicator molecules, (ii) one or more photodetectors sensitive to emission light emitted by the indicator molecules, and (iii) one or more photodetectors sensitive to excitation light reflected from the indicator as reflection light;
the signal measurement is indicative of a level of the emission light; and
the reference measurement is indicative of a level of the reflection light.

12. The method of claim 10, wherein detecting that the reference channel instability is present comprises comparing a difference between the reference measurement and a previous reference measurement to an instability threshold.

13. The method of claim 12, wherein the one or more sensor measurements further comprise a temperature measurement, and the method further comprises temperature correcting the reference measurement using at least the temperature measurement.

14. The method of claim 13, wherein detecting that reference channel instability is present comprises comparing a difference between the temperature corrected reference measurement and a previous temperature corrected reference measurement to an instability threshold.

15. The method of claim 14, wherein detecting that reference channel instability is present comprises comparing a difference between a time of the temperature corrected reference measurement and a time of the previous temperature corrected reference measurement to a time threshold.

16. The method of claim 10, wherein the analyte monitoring system further comprises a display device, and blinding the analyte monitoring system comprises to not conveying the calculated analyte level.

17. The method of claim 16, further comprising, if reference channel instability is detected, conveying a sensor check communication to the display device.

18. The method of claim 10, wherein the analyte monitoring system comprises a calibration buffer that stores one or more calibration points, and the method further comprises, if reference channel instability is detected, clearing the calibration buffer.

* * * * *